US007919699B2

(12) United States Patent
Sullivan

(10) Patent No.: US 7,919,699 B2
(45) Date of Patent: Apr. 5, 2011

(54) NANOTUBES AS MITOCHONDRIAL UNCOUPLERS

(75) Inventor: Patrick G. Sullivan, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 663 days.

(21) Appl. No.: 11/418,208

(22) Filed: May 5, 2006

(65) Prior Publication Data

US 2006/0275281 A1 Dec. 7, 2006

Related U.S. Application Data

(60) Provisional application No. 60/678,355, filed on May 6, 2005.

(51) Int. Cl.
 *B82B 1/00* (2006.01)
 *A61K 9/51* (2006.01)
(52) U.S. Cl. ......... 977/915; 977/773; 977/902; 977/904
(58) Field of Classification Search .................. None
See application file for complete search history.

(56) References Cited

U.S. PATENT DOCUMENTS

| | | | |
|---|---|---|---|
| 4,673,691 A | 6/1987 | Bachynsky | |
| 5,853,975 A * | 12/1998 | Tartaglia | 435/4 |
| 6,001,578 A * | 12/1999 | Lind et al. | 435/6 |
| 6,472,378 B2 | 10/2002 | Von Borstel | |
| 6,495,680 B1 * | 12/2002 | Gong | 540/456 |
| 6,613,875 B1 | 9/2003 | Ghadiri | |
| 6,685,730 B2 * | 2/2004 | West et al. | 607/89 |
| 2004/0023372 A1 | 2/2004 | Klein et al. | |
| 2004/0038251 A1 * | 2/2004 | Smalley et al. | 435/6 |
| 2004/0076681 A1 * | 4/2004 | Dennis et al. | 424/489 |
| 2005/0096509 A1 | 5/2005 | Olson | |

FOREIGN PATENT DOCUMENTS

WO   WO 2004/089819 A1   10/2004
WO   WO 2006/043966 A2   4/2006

OTHER PUBLICATIONS

Clark, TD et al. Self-assembling cyclic beta3-peptide nanotubes as artificial transmembrane ion channels. J. Am. Chem. Soc. 1998. 120: 651-656.*
Menon, VP et al. Fabrication and evaluation of nanoelectrode ensembles. Anal. Chem. 1995. 67: 1920-1928.*
Martin, CR. Nanomaterials: A membrane-based synthetic approach. Science. 1994. 266: 1961-1966.*
Martin, CR et al. Investigation of the transport properties of gold nanotubule membranes. J. Phys. Chem. B. 2001. 105: 1925-1934.*
Supplementary European Search Report dated Mar. 20, 2009 (Four (4) pages).
Martin et al., "The Emerging Field of Nanotube Biotechnology," Nature Reviews Drug Discovery, vol. 2, Jan. 2003, pp. 29-37.
Martin et al., "Materials Science: Expanding the Molecular Electronics Toolbox," Science, Jul. 1, 2005, vol. 309, No. 5731, pp. 67-68.
Kohli et al., "Smart Nanotubes for Biotechnology," Current Pharmaceutical Biotechnology, Feb. 2005, vol. 6, No. 1, pp. 35-47.
Nishizawa et al., "Metal Nanotubule Membranes with Electrochemically Switchable Ion-Transport Selectivity," Science (1995), vol. 268, pp. 700-702.
Miller et al., "Electroosmotic Flow in Template-Prepared Carbon Nanotub Membranes," J. Am. Chem. Soc. (2001), vol. 123, pp. 12335-12342.
Harper et al., "Mitochondrial uncoupling as a target for drug development for the treatment of obesity," Obesity Reviews, vol. 2, No. 4, 255-265, 2001.
Kurt et al., "Dinitrophenol in weight loss: the poison center and public health safety," Vet Hum Toxicol, (1986), vol. 28, pp. 574-575.
Tainter et al., "Dinitrophenol in the treatment of obesity: final report," J. Am. Med. Assoc., vol. 105, pp. 332-337, 1935.
Sullivan et al., "Mitochondrial Uncoupling as a Therapeutic Target Following Neuronal Injury," Journal of Bioenergetics and Biomembranes, Aug. 2004, vol. 36, No. 4, pp. 353-356.
Mattiasson et al., "The Emerging Functions of UCP2 in Health, Disease and Therapeutics," Antioxidants & Redox Signaling, 2006, vol. 8, Nos. 1&2, pp. 1-38.
Hall et al., *Preserving Function in Acute Nervous System Injury. In: From Neuroscience to Neurology: Neuroscience, Molecular Medicine, and the Therapeutic Translation of Neurology*, (S. Waxman, Ed.), Elsevier.Academic Press, Amsterdam, pp. 35-59, 2004.
Lipshitz et al., "Mitochondrial Damage and Dysfunction in Traumatic Brain Injury," Mitochondrion, (2005), vol. 4, pp. 705-713.
Singh, "Time Course of Post-Traumataic Mitochondrial Oxidative Damage and Dysfunction in a Mouse Model of Focal Traumatic Brain Injury: Implications for Neuroprotective Therapy," Journal of Cerebral Blood Flow & Metabolism, In Press, Epub Mar. 15, 2006.
Gao et al., "In vivo cancer targeting and imaging with semiconductor quantum dots," Nature Biotechnology, Aug. 2004, vol. 22. No. 8, pp. 969-976.

(Continued)

Primary Examiner — Allison M Ford
Assistant Examiner — Susan E Fernandez
(74) Attorney, Agent, or Firm — Crowell & Moring LLP

(57) ABSTRACT

A method of uncoupling mitochondria in a subject including administering nanotubes to the subject in a therapeutically effective amount, wherein the nanotubes are self-rectifying is provided. A method of decreasing reactive oxygen species and decreasing detrimental loading of $Ca^{2+}$ into mitochondria is provided, including administering a pharmaceutically effective amount of nanotubes into the subject. A method of reducing weight, treating cancer, reducing the effects of traumatic brain injury, or reducing the effects of ageing, in a subject including administering a pharmaceutically effective amount of nanotubes into the subject is also provided.

21 Claims, 13 Drawing Sheets

OTHER PUBLICATIONS

Han et al., "*Quantum-dot-tagged microbeads for multiplexed optical coding of biomolecules*," Nature Biotechnology, (2001), vol. 19, pp. 631-635.

Savic et al., "*Micellar Nanocotainers distribute to defined cytoplamsic organelles*," Science, (2003), vol. 300, pp. 615-618.

Sullivan et al., "*Mitochondrial Uncoupling Protein-2 Protects the Immature Brain from Excitotoxic Neuronal Death*," Annals of Neurology, (Jun. 2003), vol. 53, No. 6, pp. 711-717.

Sullivan et al., "*The Ketogenic Diet Enhances Increases Mitochondrial Uncoupling Protein Levels and Activity In Mouse Hippocampus*," Annals of Neurology, (2004), vol. 55, pp. 576-580.

Brown et al., "*Brain region-specific, age-related, alterations in mitochondrial responses to elevated calcium*," Journal of Bioenergetics and Biomembranes, (2004), vol. 36, pp. 401-406.

Jin et al., "*The Mitochondrial Uncoupling Agent 2,4-Dinitrophenol Improves Mitochondrial Function, Attenuates Oxidative Damage, and Increases White Matter Sparing in the Contused Spinal Cord*," Journal of Neurotrauma, (2004), vol. 21, pp. 1396-1404.

Korde et al., "*The uncoupling agent 2,4-dinitrophenol improves mitochondrial homeostasis following striatal quinolinic acid injections*," Journal of Neurotrauma, (2005), vol. 22, pp. 1142-1149.

Lin et al., "*The gene gun: current applications in cutaneous gene therapy*," (2000) Int. J. Dermatol., vol. 39, No. 3, pp. 161-170.

Korde, "The Mitochondrial uncoupler 2, 4-dinitrophenol attenuates tissue damage and improves mitochandrial homeostasis following transient focal cerebral ischemia", J Neurochem, (2005), vol. 94, No. 6, pp. 1676-1684.

Remington's Pharmaceutical Sciences, Mace Publishing Company, Philadelphia, Pennyslvania, 17th Ed (1985).

Charles Martin et al., The Emerging Field of Nanotube Biotechnology, Nature Reviews Drug Discovery, vol. 2, Jan. 2003, pp. 29-37.

\* cited by examiner

A

Vehicle  2,4-DNP

B

NANOTUBES AS MITOCHONDRIAL UNCOUPLERS

CROSS-REFERENCE TO RELATED APPLICATION

This application claims priority under 35 U.S.C. §119 to U.S. Provisional Application No. 60/678,355 entitled NANOTUBES AS MITOCHONDRIAL UNCOUPLERS, filed May 6, 2005, the entire content of which is hereby incorporated by reference.

FIELD OF THE INVENTION

The present invention relates to nanotubes as mitochondrial uncouplers. The present invention provides methods of mitochondrial uncoupling as well as methods of treating disease conditions and increasing weight loss by administering the nanotubes.

BACKGROUND

It is known that mitochondria control metabolism in individual cells by burning sugars and fats. Mitochondria produce a membrane potential of about 200 mV across their inner membrane by the active translocation of protons from the matrix of the mitochondria (the inside) into the inner membrane space (mitochondria have an inner an outer membrane as illustrated in FIG. 2). The translocation of protons from the matrix is due to the activity of the electron transport system, which takes electrons from a high energy state to a lower energy resulting in the reduction of oxygen to water, hence the term mitochondrial respiration since oxygen is consumed by this process. The energy released as electrons are taken from a high energy state to a lower energy state is used by this electron transport system to translocate (i.e., pump) the protons from the matrix to the inner membrane space resulting in a separation of charge (i.e., membrane potential) as well as a pH gradient across the inner membrane due to the movement of these protons.

The mitochondrial membrane potential is then "coupled" to the controlled flow of protons back into the matrix through the ATP synthase which uses this flow to phosphorylate adenosine diphosphate ("ADP") to ATP.

Chemical uncouplers of mitochondria have been used to increase the bodies basal metabolism to encourage weight loss. However, chemical uncouplers are readily toxic, as they are difficult to control. Uncontrolled uncoupling of mitochondria (i.e., dropping the mitochondrial membrane potential below about 100 mV) causes an inability to produce cellular ATP, which eventually leads to death.

Therefore, there is a need for safe, controllable, mitochondrial uncouplers that can separeate the mitochondria respiration from the production of ATP, and thus safely produce the desired effect, without harming the individual.

SUMMARY OF THE INVENTION

The present invention provides nanotubes which safely uncouple mitochondria, as the nanotubes can be prepared such that the proton channel automatically shuts down when an unsafe potential is reached.

The template method of forming nanotubes in one embodiment allows control of the dimensions of the nanotubes such that the nanotubes can be designed to have any desired dimensions as specified. By allowing manipulation of size, particularly the inner diameter of the nanotubes (as explained above), these nanotubes allow specific conductance (i.e., uncoupling threshold and resistance to proton flow) of the nanotubes. The template method further allows lining or coating the inside and outside of the nanotubes with any desired materials.

Template synthesis of nanotubes generally involves the deposition of materials (e.g., gold, alumina, silica etc.) into the cylindrical pores of mass-produced track-etched membranes (e.g., Corning Corp; Osmonics). Once the nanotubes are formed within the membrane pores, the membrane can be dissolved and the nanotubes can be captured via filtration. By altering the conditions during preparation (e.g., reducing the plating time when using the electroless plating method for creating gold nanotubes increases the inner diameter of the nanotube accordingly) the internal diameter, length and contents of the nanotube can be controlled as specified.

According to another embodiment, nanotubes made of metals and/or polymers are used to safely uncouple mitochondria, raise metabolism, and promote weight loss.

According to another embodiment, the nanotubes have a length of about 8-12 nm and a diameter of about 1-3 nm, wherein the nanotubes can cross cell membranes substantially easily, and wherein the mitochondria have a length of about 1000-5000 nm and the bilipid membrane of the mitochondria is about 8-10 nm thick.

According to a further embodiment, the nanotubes can be active only in the mitochondria. This is due to the fact that the nanotubes only act as proton channels when a significantly high potential is applied (about 130-150 mV), which is only found across the mitochondrial inner membrane in mammal cells.

In a further embodiment, the interior surface of the non-carbon based nanotubes can be doped with compounds of specific pKa such that the non-carbon based nanotube shuts off when a specific pH is reached. This allows us to take advantage of the fact that mitochondria have a pH gradient across the inner membrane as a result of the pumping of protons from the matrix across the inner membrane via the electron transport system.

In one embodiment, the nanotubes act as proton channels specifically in the mitochondria. The nanotubes acting as proton channels cause a reduction in mitochondrial membrane potentials which in turn increases basal metabolism, decreases reactive oxygen species ("ROS"), and decreases detrimental loading of $Ca^{2+}$ into mitochondria. The reason for this is that all these parameters are a function of the membrane potential such that a high mitochondrial membrane potential slows down metabolism and increases ROS formation and the uptake of $Ca^{2+}$ into mitochondria.

The nanotubes conduct protons (i.e., open and uncouple mitochondria) only when a specific potential (i.e., breakover voltage) is reached. This causes a drop in the mitochondrial membrane potential that closes the nanotube proton channel, in effect making the nanotubes self-rectifying. Therefore, nanotubes can be designed to maintain a specific mitochondrial membrane potential that can significantly increase metabolism without the possibility of toxicity since the nanotubes will not function (act as proton channels) at a mitochondrial membrane potential below the threshold for ATP production.

According to one embodiment, the dimensions of nanotubes and the materials they are made from are manipulated to accomplish safe mitochondrial uncoupling. For example, when the diameter of the nanotubes is decreased, a smaller diameter increases resistance and the conductance of protons through the nanotubes (uncouples the mitochondria electron transport from ATP production) only when the voltage reaches threshold (the mitochondrial membrane potential). These nanotubes that are highly effective for weight-loss and at the same time are substantially safe for use because they are self-rectifying.

In one embodiment, nanotubes can offer a safe and effective treatment for obesity and weight management by increasing basal metabolism by increasing mitochondrial respiration.

In another embodiment a method of uncoupling mitochondria in a subject comprising administering nanotubes to the subject in a therapeutically effective amount, wherein the nanotubes are self-rectifying is disclosed.

The nanotubes can be coated with a pKa reducing compound. The subject can be a mammal. The nanotubes have an inner diameter suitable for uncoupling mitochondria. The nanotubes have an inner diameter which allows the nanotubes to self-rectify.

The nanotubes comprise metals or polymers, wherein the metal is gold or silver, and wherein the polymers are natural polymers or synthetic polymers. The polymers are preferably selected from the group consisting of poly(vinyl alcohol), poly(esters), polyglycolide, polycaprolactone, poly(ethylene oxide), poly(butylene terephthalate), poly(hydroxyalkanoates), hydrogels, modified poly(saccharides), starch, cellulose, chitosan and combinations thereof.

In another embodiment, a method of decreasing reactive oxygen species and decreasing detrimental loading of $Ca^{2+}$ into mitochondria of a subject comprising administering nanotubes to the subject in a therapeutically effective amount, wherein the nanotubes are self-rectifying is disclosed.

The subject can be a mammal. The nanotubes have an inner diameter designed for uncoupling mitochondria. The nanotubes have an inner diameter which allows the nanotubes to self-rectify. The nanotubes comprise metals or polymers, wherein the metal is gold or silver, and wherein the polymers are natural polymers or synthetic polymers. The polymers are preferably selected from the group consisting of poly(vinyl alcohol), poly(esters), polyglycolide, polycaprolactone, poly (ethylene oxide), poly(butylene terephthalate), poly(hydroxyalkanoates), hydrogels, modified poly(saccharides), starch, cellulose, and chitosan.

In another embodiment, a method of reducing weight in a subject comprising administering a therapeutically effective amount of nanotubes to the subject, wherein the nanotubes are self-rectifying is disclosed.

The subject can be a mammal. The nanotubes have an inner diameter designed for uncoupling mitochondria. The nanotubes have an inner diameter which allows the nanotubes to self-rectify. The nanotubes comprise metals or polymers, wherein the metal is gold or silver, and wherein the polymers are natural polymers or synthetic polymers. The polymers are preferably selected from the group consisting of poly(vinyl alcohol), poly(esters), polyglycolide, polycaprolactone, poly (ethylene oxide), poly(butylene terephthalate), poly(hydroxyalkanoates), hydrogels, modified poly(saccharides), starch, cellulose, and chitosan.

In another embodiment, a method of treating cancer in an subject comprising administering a therapeutically effective amount of nanotubes to the subject, wherein the nanotubes are self-rectifying is disclosed.

The subject can be a mammal. The nanotubes have an inner diameter designed for uncoupling mitochondria. The nanotubes have an inner diameter which allows the nanotubes to self-rectify. The nanotubes comprise metals or polymers, wherein the metals are gold or silver, and wherein the polymers are natural polymers or synthetic polymers. The polymers are preferably selected from the group consisting of poly(vinyl alcohol), poly(esters), polyglycolide, polycaprolactone, poly(ethylene oxide), poly(butylene terephthalate), poly(hydroxyalkanoates), hydrogels, modified poly(saccharides), starch, cellulose, and chitosan.

In another embodiment a method of reducing the effects of traumatic brain injury in an subject comprising administering a therapeutically effective amount of nanotubes to the subject, wherein the nanotubes are self-rectifying is disclosed.

The subject can be a mammal. The nanotubes have an inner diameter designed for uncoupling mitochondria. The nanotubes have an inner diameter which allows the nanotubes to self-rectify. The nanotubes comprise metals or polymers, wherein the metals are gold or silver, and wherein the polymers are natural polymers or synthetic polymers. The polymers are preferably selected from the group consisting of poly(vinyl alcohol), poly(esters), polyglycolide, polycaprolactone, poly(ethylene oxide), poly(butylene terephthalate), poly(hydroxyalkanoates), hydrogels, modified poly(saccharides), starch, cellulose, and chitosan.

In another embodiment, a method of reducing the effects of ageing in a subject comprising administering a therapeutically effective amount of nanotubes to the subject, wherein the nanotubes are self-rectifying is disclosed.

The subject can be a mammal. The nanotubes have an inner diameter designed for uncoupling mitochondria. The nanotubes have an inner diameter which allows the nanotubes to self-rectify. The nanotubes comprise metals or polymers, wherein the metals are gold or silver, and wherein the polymers are natural polymers or synthetic polymers. The polymers are preferably selected from the group consisting of poly(vinyl alcohol), poly(esters), polyglycolide, polycaprolactone, poly(ethylene oxide), poly(butylene terephthalate), poly(hydroxyalkanoates), hydrogels, modified poly(saccharides), starch, cellulose, and chitosan.

In another embodiment, a pharmaceutical composition is disclosed, wherein the pharmaceutical composition comprises nanotubes in a pharmaceutically acceptable carrier, and wherein the pharmaceutical composition is administered to an subject by (i) intravenous delivery, (ii) ingestion, (iii) particle bombardment via a gene gun, or (iv) patch or gel application to the dermis.

In another embodiment a method of reducing the effects spinal cord injury in a subject comprising administering a therapeutically effective amount of nanotubes to the subject, wherein the nanotubes are self-rectifying is disclosed.

In another embodiment, a method of reducing the effects of stroke in a subject comprising administering a therapeutically effective amount of nanotubes into the subject, wherein the nanotubes are self-rectifying is disclosed.

DETAILED DESCRIPTION OF THE INVENTION

Definitions

Figure 1:
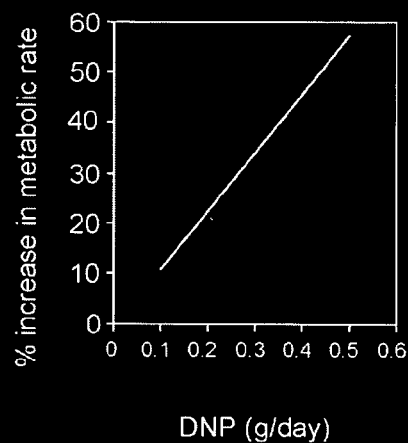
FIG. 1 shows two line graphs indicating that 2,4-DNP increases metabolism and weight loss in a dose-dependent manner in humans.
Figure 1:
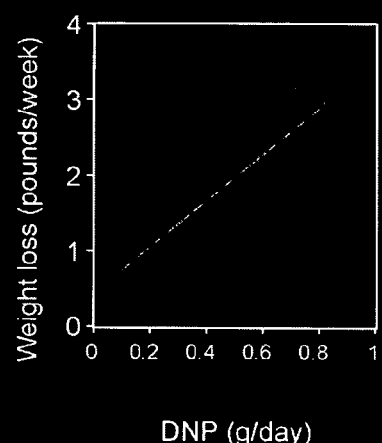

In accordance with this detailed description, the following abbreviations and definitions apply. It must be noted that as used herein, the singular forms "a", "an", and "the" include plural referents unless the context clearly dictates otherwise. Thus, for example, reference to "compounds" includes a plurality of such compounds and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless otherwise stated, the following terms used in the specification and claims have the meanings given below:

"Pharmaceutically acceptable carrier" means a carrier that is useful in preparing a pharmaceutical composition that is generally safe, non toxic and neither biologically nor otherwise undesirable, and includes a carrier that is acceptable for veterinary use as well as human pharmaceutical use. "A pharmaceutically acceptable carrier" as used in the specification and claims includes both one, and more than one, such carrier.

"Treating" or "treatment" of a disease includes:
(1) preventing the disease, i.e., causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" or "pharmaceutically effective amount" means the amount of a compound that, when administered to a mammal, is sufficient to uncouple mitochondria, and/or sufficient to decreasing reactive oxygen species and decreasing detrimental loading of $Ca^{2+}$ into mitochondria. A "therapeutically effective amount" or "pharmaceutically effective amount" also means and amount sufficient for treating a disease and sufficient to effect such treatment for the disease. The "therapeutically effective amount" will vary depending on the compound, the disease and its severity and the age, weight, etc., of the mammal to be treated. A "therapeutically effective amount" also may refer to an amount sufficient to cause weight loss.

"Pharmaceutically acceptable salt" refers to pharmaceutically acceptable salts of scopolamine which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Optional" or "optionally" means that the subsequently described event or circumstance may, but need not, occur, and that the description includes instances where the event or circumstance occurs and instances in which it does not.

The term "individual" is a vertebrate, preferably a mammal. Mammals include, but are not limited to, humans, rodents (i.e., mice, rats, and hamsters), farm animals, sport animals and pets. In a preferred embodiment, the individual is a mammal and more preferably, a human.

As used herein, the term "introducing" means providing or administering to an individual. Methods of introducing nanotubes into individuals are well known to those of ordinary skill in the art and include, but are not limited to, injection, intravenous or parenteral administration. Single, multiple, continuous or intermittent administration can be effected.

As used herein, the term "nanotube" includes structures formed from various materials using a generally known template method. Further, nanotubes include structures of various shapes having dimensions smaller than about 1000 nm, preferably smaller than about 100 nm, more preferably smaller than about 50 nm, and most preferably smaller than about 20 nm. In a preferred embodiment, these nanostructures are hollow tube-like and/or solid wire-like structures.

As used herein, the term "self-rectifying" refers to the ability of the nanotubes to stop acting as a proton channel once the mitochondrial membrane potential is lowered to a set threshold.

Nanotubes

The present invention relates to nanotubes used as mitochondrial uncouplers-in the body. Previous mitochondrial uncouplers, such as 2,4-DNP, are often toxic as they decrease and/or stop the production of ATP in the body. The nanotubes of the present invention act are safe, as they do not adversely affect production of ATP and utilize a different uncoupling mechanism than the mechanism of the chemical uncouplers.

The presently disclosed nanotubes act as self-rectifying proton channels across the mitochondrial inner membrane. When the membrane potential reaches a certain point, the nanotubes shut off the proton flow. This mechanism is similar to that of an electrical circuit, as the flow across mitochondrial membranes follows the principles of Ohm's law. According to Ohm's law, V (voltage)=I (current) R (resistance) (i.e., if one reduces R, I will increase). In the case of mitochondria, the voltage is the separation of protons across the inner membrane due to mitochondrial respiration (i.e., electron transport system activity) and the current is the flow of protons back across the inner membrane back into the matrix (i.e., flow of protons through the ATP synthase or nanotubes).

Under normal conditions, resistance ("R") is set by the demand for ATP to be produced by mitochondria. In the case of uncontrolled chemical uncoupling, resistance is a function of the amount of uncoupler that is present. Thus, if the dosage is too high, all resistance is abolished resulting in maximum current flow. In the case of the presently disclosed nanotubes, resistance can be adjusted by changing the inner diameter of the nanotube and/or by "doping" the inside of the nanotubes with compounds of specific pKas. The present nanotubes act as proton channels which allow protons to flow back into the matrix across the inner mitochondrial membrane due to the voltage (i.e., separation of charge) that is present.

The flow of protons can be controlled by increasing or decreasing the inner diameter the nanotubes such that they will only allow a flow of protons only when a threshold voltage is reached. By decreasing the inner diameter of the nanotubes, the amount of voltage required to "push" protons through the nanotube is increased, such that only when the required voltage (or higher) is applied will protons flow through the nanotubes back into the matrix. This in effect makes the nanotubes self-rectifying in that they will not act as proton channels once the mitochondrial membrane potential is lowered to a set threshold. This failsafe mechanism will activate regardless how many tubes are present, because they will only act as proton channels when the threshold voltage is present.

Thus, the present nanotubes are safe to administer as mitochondrial uncouplers, as they cause the mitochondnal uncoupling to stop prior to any adverse effects.

The nanotubes, acting as proton channels, cause a reduction in mitochondrial membrane potentials, which in turn increases basal metabolism, decreases reactive oxygen species ("ROS"), and decreases detrimental loading of $Ca^{2+}$ into mitochondria.

The present nanotubes may be made of metals, polymers, semiconductors, carbons, and other materials. Preferably, the nanotubes are made of any elemental metal that will plate or coat the walls of the template used, including, but not limited to, gold, copper, platinum, nickel and silver. Most preferably, the nanotubes are made of gold, as gold is inert and does not cause any inflammatory response in the body.

The nanotubes can be made from polymers. These polymers can be natural or synthetic and can include poly(vinyl alcohol), poly(esters), polyglycolide, polycaprolactone, poly(ethylene oxide), poly(butylene terephthalate), poly(hydroxyalkanoates), hydrogels, modified poly(saccharide)s such as starch, cellulose, and chitosan.

Different characteristics of the nanotubes, such as the effective half-life (i.e., how long the nanotube will be stable in the body), can be altered by changing the percent composition of the different polymers to achieve a desired effect. See Martin C. R., et al., *Materials science: Expanding the Molecular Electronics Toolbox, Science,* 2005 July 1, 309 (5731):67-8; Kohli, P., et al., *Smart Nanotubes for Biotechnology, Current Pharmaceutical Biotechnology,* 2005 February, 6(1):35-47; Martin C. R., *Nanomaterials: A Membrane-Based Synthetic Approach,* Science (1994), 266, 1961-1966; and Martin C. R., *The Emerging Field of Nanotube Biotechnology,* Nature Reviews Drug Discoveries (2003), 2 29-37.

Copolymers of poly(ester)s based on polylactide, polyglycolide, and polycaprolactone can also be used to make the nanotubes. Multiblock copolymers of poly(ethylene oxide) and poly(butylene terephthalate) can also be used to make the nanotubes. The poly(esters) can be based on polylactide.

The use of nanotubes as proton channels in mitochondria can circumvent the toxic side effects of chemical uncouplers and safely increase metabolism (and promote weight loss). Nanotubes act as high-conductance proton channels, mimicking chemical uncouplers, without substantially any chance of toxicity. This can be accomplished by the use and manufacturing of voltage-dependent nanotubes that act as effective proton diodes and rectifiers in the mitochondrial membrane. The nanotubes can conduct protons only when a specific potential (i.e., breakover voltage) is reached which causes the nanotubes to act as proton channels which will reduce mitochondrial membrane potential to a point that will close the nanotube proton channel.

As discussed supra, one reason that the present nanotubes are safe for use in the body is the mechanism of conducting protons only when a specific potential (i.e., breakover voltage) is reached. This characteristic of the nanotubes causes a drop in the mitochondrial membrane potential that closes the nanotube proton channel, in effect making the nanotubes self-rectifying. Therefore, nanotubes can be designed to maintain a specific mitochondrial membrane potential that can significantly increase metabolism, substantially without the possibility of toxicity, because the nanotubes can be designed to not function at a mitochondrial membrane potential below the threshold for ATP production. Additionally, the nanotubes (i.e., proton channels) can only function in the mitochondria, because a proton gradient of about 120-220 mV does not exist anywhere else in mammalian cells.

Nanotubes can be designed to maintain a specific mitochondrial membrane potential that can significantly increase metabolism without the toxicity associated with reducing mitochondrial membrane potential below the threshold for ATP production. Nanotube proton channels can function only at the mitochondria in the cells of in an individual because a proton gradient of similar magnitude does not exist anywhere else in an individual's cell.

The inner diameter ("i.d.") of the nanotubes can be altered until the desired conductance is realized. It is well known that reducing the nanotube i.d. also reduces the conductance (increases the resistance) of the channel to proton flow in accordance with Ohms law. See Nishizawa M., et al., *Metal Nanotubule Membranes with Electrochemically Switchable Ion-Transport Selectivity,* Science (1995), 268, 700-702; Miller S. A., et al., *Electroosmotic flow in template-prepared carbon nanotube membranes,* J. Am. Chem. Soc (2001). 123, 12335-12342; and Martin, C. R., *Nanomaterials: A Membrane-Based Synthetic Approach,* Science (1994), 266, 1961-1966.

Further, the proton conductance and selectivity of the nanotubes can be adjusted and/or increased by using compounds of specific pKa including specific chemisorbed amino acids. These amino acids can be incorporated into the inner walls of the nanotubes during template synthesis. Depending on the chemical properties of the amino acids, nanotubes that are highly-selective for protons in addition to being pH sensitive can be created.

Generally, a pH difference of about 0.5 exists across the inner mitochondrial membrane. When the interior surface of the nanotubes is coated (i.e., "doped") with compounds of specific pKa such that the nanotube shuts off when this pH gradient reaches a certain level such that the compound will no longer be protonated and cease to conduct protons. This acts as a second failsafe device, in addition to controlling proton conductance. Based on the pH gradient across the mitochondrial inner membrane, any compound with a pKa in the range of 4 to 5 (in $H_2O$ at ~37° C.) and that has a small enough molecular weight that it can fit into the nanotube, would be ideal for this application. Ion selectivity can also be adjusted by doping the inside of the nanotubes with compounds of the opposite charge of the ion selected.

Preparation of Nanotubes

A template method of forming the nanotubes generally includes (a) immersing a template membrane into methanol, (b) immersing the template membrane into a solution having $SnCl_2$ and trifluoroacetic acid, (c) immersing the template membrane in methanol twice, (d) immersing the template membrane in an aqueous ammonical $AgNO_3$ solution or any aqueous solution containing the material you wish to use for plating of the membrane, (e) immersing the template membrane in methanol, (f) placing the template membrane in a gold-plating bath, the gold-plating bath having commercial gold plating solution, (g) adjusting the pH of the gold-plating bath to about 10 by drop-wise addition of $H_2SO_4$ while stirring, (h) placing the template membrane in the gold-plating bath for different periods of time to obtain hollow tube-like structures of different inside diameters. $CH_2Cl_2$ is added to dissolve the membrane.

In one embodiment, the template method of forming the nanotubes includes (a) immersing a template membrane into methanol for about 2-10 minutes, (b) immersing the template membrane into a solution having $SnCl_2$ and trifluoroacetic acid for about 30-60 minutes, (c) immersing the template membrane in methanol twice for about 1-5 minutes each time, (d) immersing the template membrane in an aqueous ammonical $AgNO_3$ solution for about 2-10 minutes, (e) immersing the template membrane in methanol for about 2-10 minutes, (f) placing the template membrane in a gold-plating bath at a temperature of about 2-10° C., the gold-plating bath having commercial gold plating solution, which typically includes $Na_2SO_3$, formaldehyde, and $NaHCO_3$, (g) adjusting the pH of the gold-plating bath to about 10 by drop-wise addition of $H_2SO_4$ while stirring, (h) placing the template membranes in the gold-plating bath for different periods of time to obtain hollow tube-like structures of different inside diameters. $CH_2Cl_2$ is added to dissolve the membrane.

Preferably, in another embodiment, the template method of forming the nanotubes includes (a) immersing a template membrane into methanol for about 2-10 minutes, preferably for about 5 minutes, (b) immersing the template membrane into a solution having about 0.025 M $SnCl_2$ and 0.07 M trifluoroacetic acid for about 30-60 minutes, preferably for about 45 minutes, (c) immersing the template membrane in methanol twice for about 1-5 minutes each time, preferably for about 2.5 minutes each time, (d) immersing the template membrane in a 0.029 M aqueous ammonical $AgNO_3$ solution for about 2-10 minutes, preferably for about 5 minutes, (e) immersing the template membrane in methanol for about 2-10 minutes, preferably for about 5 minutes, (f) placing the template membrane in a gold-plating bath at a temperature of about 2-10° C., preferably at a temperature of 5° C., the gold-plating bath having commercial gold plating solution, which typically includes 0.127 M $Na_2SO_3$, 0.625 M formaldehyde, and 0.025 M $NaHCO_3$, (g) adjusting the pH of the gold-plating bath to about 10 by drop-wise addition of 0.5 M $H_2SO_4$ while stirring, (h) placing the template membranes in the gold-plating bath for different periods of time to obtain hollow tube-like structures of different inside diameters. $CH_2Cl_2$ is added to dissolve the membrane.

In another embodiment, a polycarbonate track etched membrane (e.g., from Sterlitech™ Corporation) is immersed in methanol for 5 minutes. Substantially all of the methanol is drained off and the membrane is immersed in a solution which is about 0.025 M $SnCl_2$ and about 0.07 M trifluoroacetic acid. Both the chemicals should be added in equal volumes. The membrane is kept in the $SnCl_2$ and trifluoroacetic acid solution for about 30-60 minutes. The solution is then drained off and the membrane is immersed in methanol. The immersion of the membrane in methanol is to remove any residual $SnCl_2$ or trifluoroacetic acid. The membrane is then immersed in an aqueous ammonical $AgNO_3$ solution. The membrane is placed in a solution containing substantially equal volumes of $Na_2SO_3$, $NaHCO_3$, HCOOH, and a commercial gold plating solution. The solution should be maintained at a temperature of about 5° C. The membranes are kept in the gold-plating solution for 3, 6, 9 or 24 hours. The inner diameter of the tubes changes with the plating time. After the respective amount of time, the solution is drained-off and $CH_2Cl_2$ or other similar solvent is added to dissolve the membrane. The solution is then centrifuged to separate aggregated nanotubes. The solution is then removed leaving the aggregated nanotubes behind. PEG is added to the aggregated nanotubes such that the PEG coats the nanotubes causing the aggregated nanotubes to separate such that substantially individual nanotubes coated with PEG are available in water or similar solvent as a solution. The mixture is then vortexed (i.e., mixed vigorously using a genie vortexer or other similar mixer) to aid the coating of the nanotubes with PEG thereby increasing the availability of the nanotubes in solution. The mixture is then filtered to remove any particulate matter. The filtered nanotubes are then pelleted by centrifugation, the supernatant removed and the pellet re-suspended in ethanol to remove excess PEG. The nanotubes are then pelleted again by centrifugation, the supernatant removed and the pellets are re-suspended in sterile water and stored at about 4° C.

The plated membranes obtained from the method described above can then be placed in a solution of histidine (or any compound one wishes to us to dope the inside of the nanotubes). The plated membranes are left in the histidine solution for 24 hours to allow the histidine to coat the inner walls of the plated membranes having the nanotubes. The coated membranes can be removed and placed in $CH_2Cl_2$ and sonicated, so as to dissolve the membrane. PEG can be added to the resultant solution which will coat the outside of the nanotubes making them soluble. The PEG solution can be centrifuged so that the nanotubes settle at the bottom. The PEG solution can be removed so that the nanotubes can be collected. Ethanol ("EtOH") can be added allowing the tubes to be suspended in a sterile medium. The solution can be drained off after centrifuging and EtOH can be added to obtain histidine coated nanotubes.

PEG is added to the outside of the nanotubes in order to allow them to become soluble in solution, prior to filtration. Nanotubes that are manufactured in the absence of PEG do not make it through the filtration process.

Further, the proton conductance of the nanotubes can be adjusted by using compounds of specific pKa including specific chemisorbed amino acids. These amino acids can be incorporated into the inner walls of the nanotubes during template synthesis. Depending on the chemical properties of the amino acids nanotubes that are highly-selective for protons in addition to being pH sensitive can be created. Generally, a pH difference of about 0.5 exists across the inner mitochondrial membrane. When the interior surface of the nanotubes is doped with compounds of specific pKa, that the nanotubes shut off when a specific pH is reached.

Any weak acid that has a pKa of 4-5 in $H_2O$ at about 37° C. and has molecules that can penetrate the i.d. of the nanotubes, can be used as proton conductance adjusting compounds. In a preferred embodiment, these proton conductance adjusting compounds are selected from the group consisting of asparate, glutamate, and combinations thereof.

Any organic solvent that can dissolve the template used in the template method of forming nanotubes can be used. In a preferred embodiment, the organic solvent may be methanol, methylene chloride, or combinations thereof.

Uses of Nanotubes as Mitochondrial Uncouplers

The present nanotubes may be used to treat or manage any condition that is related to, or may be affected by, mitochondrial uncoupling. Moreover, any condition caused by an increase in ROS and/or an increase in $Ca^{2+}$ can be treated and/or the effects therefrom can be reduced, by administering the nanotubes of the present invention.

The following diseases or conditions are exemplary and are not meant to limit the conditions caused by or aggravated by mitochondrial uncoupling.

Obesity/Weight Control

According National Institute of Health ("NIH"), recent figures from the Centers for Disease Control and Prevention show that 65 percent of U.S. adults—or about 129.6 million people—are either overweight or obese. In addition to decreasing quality of life and increasing the risk of premature death, obesity and overweight individuals cost the United States of America ("U.S.") an estimated $117 billion in direct medical costs and indirect costs, such as lost wages due to illness.

Obesity is in epidemic proportions and is recognized as one of the most important health issues facing the U.S. Numerous research studies have directly shown that obesity increases the risk of developing a number of health conditions, including type 2 diabetes, hypertension, coronary heart disease, ischemic stroke, colon cancer, post-menopausal breast cancer, endometrial cancer, gall bladder-disease, osteoarthritis, and obstructive sleep apnea. In fact, obesity-related disease is now only second to smoking as the cause of premature death in the U.S. (Centers for Disease Control).

In the 1930s it was recognized that increasing the body's basal metabolism using mitochondrial uncouplers directly resulted in steady and rapid weight loss. Chemical mitochondrial uncouplers were found to significantly increase weight loss in a dose-dependent manner by reducing membrane potential and increasing respiration in mitochondria (ie., increasing basal metabolism). See Harper, J. A., et al., (2001), *Mitochondrial uncoupling as a target for drug development for the treatment of obesity*, Obesity Reviews 2 (4), 255-265; and Kurt, T. L., et al., *Dinitrophenol in weight loss: the poison center and public health safety*, Vet Hum Toxicol 28, 574-5 (1986). This mechanism effectively uncouples mitochondrial adenosine triphosphate ("ATP") production from electron transport (i.e., mitochondrial respiration), which results in foodstuffs being turned into heat instead of being used as an energy source or being stored as fat. In effect, chemical uncouplers increase basal metabolism which in turn results in weight loss (See FIG. 1).

The chemical mitochondrial uncoupler 2,4-dinitrophenol ("2,4-DNP") was sold over the counter around the 1930s as a weight-loss supplement. FIG. 1 shows two line graphs indicating that 2,4-DNP increases metabolism and weight loss in a dose-dependent manner in humans. In the right panel of FIG. 1 the linear increase in metabolism as a function of 2,4-DNP dosage is demonstrated. The left panel of FIG. 1 demonstrates that as the dose of 2,4-DNP is increased, which increases metabolism, results in a very linear increase in weigh loss regardless of diet or changes in lifestyle. See Tainter M. L., et al., (1935), *Dinitrophenol in the treatment of obesity*: final report, J. Am. Med. Assoc 105, 332-337.

However, 2,4-DNP was pulled from the marked by the Food and Drug Administration ("FDA") as people were routinely overdosing on the compound in an effort to increase the rate of their weight loss (reviewed in Kurt, T. L., et al., *Dinitrophenol in weight loss: the poison center and public health safety*, Vet Hum Toxicol 28, 574-5 (1986)).

The toxicity of 2,4-DNP stems from the uncoupling mechanism utilized. Chemical uncouplers, such as 2,4-DNP, are toxic due to the mechanism by which chemical uncouplers function. These chemical uncouplers are often are weak acids that become protonated (i.e., take up a proton) due to their pKa in the inner membrane space of the mitochondria, which is more acidic than the matrix. Protonated chemical uncouplers cross the inner membrane where they release the proton back into the more basic matrix then they cross back into the inner membrane space and the cycle continues until the pH gradient and membrane potential is completely dissipated.

Overdosing with chemical uncouplers was prevalent because complete or excessive uncoupling of mitochondria (i.e., dropping the mitochondrial membrane potential below about 100 mV) causes an inability to produce cellular ATP, which eventually leads to death. See Sullivan, P. G., et al., (2004), *Mitochondrial Uncoupling as a Therapeutic Target Following Neuronal Injury*, Journal of Bioenergetics and Biomembranes, 36(4), 353-356; and Mattiasson, G., et al., (2006), *The Emerging Roles of UCP2 in Health and Disease*, Antioxidants and Redox Signaling, 8(1-2), 1-38.

Nanotubes can offer a safe and effective treatment for obesity and weight management by safely increasing basal metabolism. The present nanotubes conduct protons only when a specific potential is reached. Nanotubes can be designed to maintain a specific mitochondrial membrane potential that can significantly increase metabolism without the possibility of toxicity. In contrast to the use of nanotubes as uncouplers, chemical uncouplers significantly increase weight loss in a dose-dependent manner by reducing membrane potential and increasing respiration in mitochondria. This uncouples ATP production from electron transport which results in caloric intake being turned into heat and not an energy source.

The nanotubes can be manufactured to increase metabolism and/or weight loss by altering the range of potentials that open and close the channel, decreasing the holding potential in obese patients to maximize metabolism and weight loss.

The nanotubes may be modified to create a desired effect. Designer nanotubes can be manufactured to increase or decrease metabolism accordingly by altering the range of potentials that open or close the proton channels. For example, by decreasing the holding potential in obese patients, metabolism and weight loss can be maximized.

CNS Disorders/TBI

Generally, chemical uncouplers such as 2,4-DNP and carbonyl cyanide 4-trifluoromethoxy phenylhydrazone ("FCCP") are neuroprotective, following central nervous system ("CNS") injuries such as traumatic brain injury, SCI, stroke, Parkinson's disease, etc. Without wishing to be bound by theory, the mechanism of action most likely involves a reduction in mitochondrial $Ca^{2+}$ loading and ROS production following such an injury. Both are linked to the mitochondrial membrane potential such that a high membrane potential increases mitochondrial $Ca^{2+}$ uptake and ROS production. For example, by increasing the mitochondrial membrane potential by about 30 Mv, the uptake of $Ca^{2+}$ is increased about ten fold while also maximizing ROS production due to decreased electron transport (stalled) which increases the slippage of electrons to molecular oxygen. In contrast, by decreasing the mitochondrial membrane potential the $Ca^{2+}$ loading is reduced along with reduced production of ROS. The toxicity of chemical uncouplers limits their potential for therapeutic use in individuals, which is compounded by the altered and dynamic changes in drug metabolism that occurs following CNS injuries.

Nanotubes can offer the benefits of uncoupling and reducing membrane potential following CNS injuries, without the toxicity associated with chemical uncouplers. Furthermore, any alteration in metabolism following CNS injuries which would affect the ability of the body to metabolize chemical agents would not alter the efficacy of nanotubes.

Nanotubes can offer effective therapy for several neurological disorders in which mitochondria have been demonstrated to play a pivotal role including, but not limited to, traumatic brain injury, SCI, stroke, Alzheimer's disease, and Huntington's disease.

Traumatic brain injury ("TBI") is a serious health care problem in the United States with more than 400,000 individuals hospitalized each year and an estimated cost of greater than 25 billion dollars. There is an enormous focus on the development and discovery of neuroprotective and/or pro-regenerative agents, which may have clinical relevance following TBI.

Neuronal degeneration following TBI is believed to evolve in a biphasic manner consisting of the primary mechanical insult and a progressive secondary necrosis. It is believed that alterations in excitatory amino acids ("EAA"), increased oxidative stress, and the disruption of $Ca^{2+}$ homeostasis are major factors contributing to the ensuing neuropathology. See Hall, E. D., et al., *Preserving Function in Acute Nervous System Injury. In: From Neuroscience to Neurology: Neuroscience, Molecular Medicine, and the Therapeutic Translation of Neurology*, (S. Waxman, Ed.), Elsevier/Academic Press, Amsterdam, pp. 35-59, 2004; Sullivan, P. G., et al., (2004), *Mitochondrial Uncoupling as a Therapeutic Target Following Neuronal Injury*, Journal of Bioenergetics and Biomembranes, 36(4), 353-356; Lipshitz, J., et al., (2005), *Mitochondrial Damage and Dysfunction in Traumatic Brain Injury*, Mitochondrion, 4, 705-713; Mattiasson, G., et al., (2005), *The Emerging Roles of UCP2 in Health and Disease*, Antioxidants and Redox Signaling, 8, 1-38.

Mitochondria play a key role in the cell death cascade, and mitochondrial dysfunction has been directly linked to EM-mediated neurotoxicity. This dysfunction is directly related to $Ca^{2+}$ ions that alter mitochondrial function and increase ROS production. Following TBI, there is a significant loss of mitochondrial homeostasis, resulting in increased mitochondrial ROS production and disruption of synaptic homeostasis, implicating a pivotal role for mitochondria in the sequelae of TBI-related neuropathology.

It has been demonstrated in the past that mitochondrial dysfunction is a pivotal link in the neuropathological sequelae of brain injury. See Singh, I. N., et al., (2006), *Time Course of Post-Traumatic Mitochondrial Oxidative Damage and Dysfunction in a Mouse Model of Focal Traumatic Brain Injury: Implications For Neuroprotective Therapy*, Journal of Cerebral Blood Flow & Metabolism, (In Press, Epub Mar 15, 2006); Hall, E. D., et al., *Preserving Function in Acute Nervous System Injury. In: From Neuroscience to Neurology: Neuroscience, Molecular Medicine, and the Therapeutic Translation of Neurology*, (S. Waxman, Ed.), Elsevier/Academic Press, Amsterdam, pp. 35-59, 2004; Sullivan, P. G., et al., (2004), *Mitochondrial Uncoupling as a Therapeutic Target Following Neuronal Injury*, Journal of Bioenergetics and Biomembranes, 36(4), 353-356; Lipshitz, J., et al., (2005), *Mitochondrial Damage and Dysfunction in Traumatic Brain Injury*, Mitochondrion, 4, 705-713; Mattiasson, G., et al., (2005), *The Emerging Roles of UCP2 in Health and Disease*, Antioxidants and Redox Signaling, 8, 1-38.

TBI-induced glutamate release increases mitochondrial $Ca^{2+}$ cycling/overload ultimately leading to mitochondrial dysfunction. Loss of mitochondrial homeostasis, increased mitochondrial ROS production, as well as disruption of synaptic homeostasis, occur following TBI.

Extrinsic mitochondrial uncouplers are compounds that facilitate the movement of protons from the mitochondrial inner-membrane space into the mitochondrial matrix. Intrinsic uncoupling can be mediated via the activation of endogenous mitochondrial uncoupling proteins ("UCP") which utilize free fatty acids to translocate protons. This short circuit "uncouples" the pumping of protons out of the matrix via the electron transport system ("ETS") from the flow of protons through the ATP synthase and results in a coincidental reduction in the mitochondrial membrane potential. Long-term complete uncoupling of mitochondria would be detrimental, since it result in a loss in the ability to maintain ATP levels by mitochondria, whereas a transient or "mild uncoupling", could confer neuroprotection. Mild uncoupling during the acute phases of TBI-induced excitotoxicity would reduce mitochondrial $Ca^{2+}$ uptake (cycling) and ROS production, as both are $\Delta\Psi$-dependent. Consistent with these ideas, rats administered a mitochondrial uncoupler post-injury (5 min) have less tissue loss, improved behavioral outcomes and demonstrate a reduction in mitochondrial oxidative damage, $Ca^{2+}$ loading and dysfunction following TBI (See FIG. 2).

Although the mechanisms contributing to ischemic neuronal degeneration are myriad, mitochondrial dysfunction is now recognized as a pivotal event that can lead to either necrotic or apoptotic neuronal death. See Korde, A. S., *The mitochondrial uncoupler 2,4-dinitrophenol attenuates tissue damage and improves mitochondrial homeostasis following transient focal cerebral ischemia*, (2005) J Neurochem, 94(6):1676-84. Further, it has been shown that 2,4-DNP reduces infarct volume approximately 40% in a model of focal ischemia-reperfusion injury in the rat brain. See id.

However, as discussed above, chemical uncouplers such as 2,4-DNP can uncouple uncontrollably to the point of causing death. Therefore, nanotubes can be used to achieve the same beneficial effects after TBI related injuries such as have less tissue loss, improved behavioral outcomes and demonstrate a reduction in mitochondrial oxidative damage, $Ca^{2+}$ loading and dysfunction following TBI, without any danger of toxicity.

Cancer

Nanotubes can also be highly effective for the treatment of various cancers. Present treatment strategies utilize drugs or radiation that are toxic to replicating cells in the hope that the cancer cells can be kept in check. Such untargeted treatments are not highly effective and contribute to significant side effects due to damage to other proliferating non-cancerous cells.

Recent technology enables targeting and labeling of cancerous cells very specifically in vivo using nanosphere technology. See Gao, X., et al., *In vivo targeting and imaging with semiconductor quantum dots*, (2004) Nature Biotechnology, 22(8), 969-976; Han, M., et al., *Quantum-dot-tagged microbeads for multiplexed optical coding of biomolecules*, (2001) Nature Biotechnology, 19, 631-635; and Savic, R., et al., *Micellar Nanocotainers distribute to defined cytoplamsic organelles*, (2003) Science, 300, 615-618. With such targeting and labeling of cancerous cells possible, nanotubes can be specifically delivered directly to such targeted and labeled cancerous cells. Nanotubes may be designed to reduce membrane potential to a level that would result in the death of the targeted and labeled cancerous cells from the inside out. Nanotubes that can act as non-specific channels that when opened by the mitochondrial membrane potential, can result in the rapid swelling and bursting of the mitochondria can also be designed. This would release pro-apoptotic proteins from the mitochondria and kill the cancerous cell from the inside.

Organism Life Span

Endogenous uncoupling proteins (UCP) have recently been shown to increase the life-span of flies. It has also been demonstrated that chemical uncouplers as well as endogenous activation of UCP are neuroprotective in seizure models and may play a role in seizure reducing epilepogenesis. See Sullivan, P. G., et al., *Mitochondrial uncoupling protein-2 protects the immature brain from excitotoxic neuronal death*, (2003) Annals of Neurology, 53, 711-717; Sullivan, P. G., et al., *The Ketogenic Diet Enhances Increases Mitochondrial Uncoupling Protein Levels And Activity In Mouse Hippocampus*, (2004) Annals of Neurology, 55, 576-580; Brown, M. B., et al., *Brain region-specific, age-related, alterations in mitochondrial responses to elevated calcium*, (2004) Journal of Bioenergetics and Biomembranes, 36, 401406; Jin, Y., et al., *The Mitochondrial Uncoupling Agent 2,4-Dinitrophenol Improves Mitochondrial Function, Attenuates Oxidative Damage, and Increases White Matter Sparing in the Contused Spinal Cord*, (2004) Journal of Neurotrauma, 21, 1396-1404; and Korde, A. S., et al., *The uncoupling agent 2,4-dinitrophenol improves mitochondrial homeostasis following striatal quinolinic acid injections*, (2005) Journal of Neurotrauma, 22, 1142-1149.

Administration of Nanotubes

The nanotubes can be administered to an individual in a variety of ways well known in the art and is not limited to any particular technique.

In one embodiment, the nanotubes can be administered to an individual by wrapping the nanotubes in lipid microspheres/tubes. Once the nanotubes are surrounded by the lipid spheres, they become lipid soluble and can be injected (i.e., intravenous delivery) or ingested for administration to an individual. The nanotubes can be active only where a proton gradient of >140 mV is present (i.e., at the mitochondrial membrane). Therefore, the delivery of the nanotubes does not have to be targeted specifically to the mitochondria.

In another embodiment, the nanotubes can be administered to an individual by attaching the nanotubes to viral proteins for delivery. For example, attachment of the nanotube to the trans-activator of the transcription ("Tat") peptide not only allows for entry into cells, but also specifically targets the nanotubes to the mitochondria due to the positive charge on the Tat peptide.

In another embodiment, the nanotubes, e.g., the gold nanotubes, can be administered to the individual via particle bombardment. This technique is very simple and has been used for vaccinations. See Lin, M. T., et al., *The gene gun: current applications in cutaneous gene therapy*, (2000) Int. J. Dermatol., 39(3):161-70. Particle bombardment uses a "gene gun" to deliver the gold nanotubes using a shockwave. This allows for substantially precise placement of the nanotubes into various layers of the skin or muscle depending on the pressure used to generate shockwave.

In another embodiment, the nanotubes can be administered to the individual by patch or gel application to the dermis. Given the size of nanotubes this is a simple approach to delivery of the nanotubes over a specific time-period. The patch or gel application to the dermis also allows for specific dosage and delivery of the nanotubes by varying the release of the nanotubes from the patches or gel into the dermis (e.g., a nicotine patch).

In another embodiment, the outside surface of the nanotubes is coated with polyethylglycol ("PEG"). The PEG coated nanotubes can be easily administered to the individual regardless of the route of administration since PEG coating of the nanotubes makes them water soluble and able to readily cross the blood brain barrier in mammals. This coupled with the fact that the dosage needed to cause an effect is small should allow efficient uptake via oral administration (e.g., capsules, tablets, suspension of nanotubes).

A therapeutically effective amount or dosage is administered to the animal. Based on preliminary data in rodents this therapeutically effective dosage is in the range of at least about 0.1 mg/Kg, preferably about 1 to 100,000 mg/kg, more preferably about 2 to 10,000 mg/Kg, and most preferably about 2.5 to 5,000 mg/Kg. As the nanotubes are self-rectifying, once the lowest effective dosage is reached (i.e., the dosage that causes the desired or targeted increase in metabolism) higher dosages will have no further effect.

The nanotubes are present in the compositions and formulations in an amount sufficient to act as mitochondrial uncouplers and/or treat, manage and/or prevent a disease condition. The nanotubes are effective over a wide dosage range and are generally administered in a pharmaceutically or therapeutically effective amount. The therapeutic dosage of the nanotubes will vary according to, for example, the particular use for which the treatment is made, the manner of administration of the nanotubes, the health and condition of the patient, and the judgment of the prescribing physician. For intravenous administration, the dose will typically be in the range of about 1.0-10.0 mg/kg. Due to an inevitable decrease in absorbance of the dosage of nanotubes from a gastrointestinal tract, the dosage would have to be increased about 5 to 10 fold when the nanotubes are administered in any oral form. Effective doses can be readily extrapolated from dose-response curves derived from in vitro or animal model test systems.

The actual amount of the nanotubes administered will depend on a number of factors, such as the severity of the disease, the age and relative health of the subject, and the route and form of administration, and other factors.

The amount administered to the patient will vary depending upon what is being administered, the purpose of the administration, such as prophylaxis versus therapy, the state of the patient, the manner of administration, and the like. In therapeutic applications, nanotubes are administered to a patient already suffering from symptoms and/or a condition in an amount sufficient to cure or at least partially arrest the symptoms and complications. An amount adequate to accomplish this is defined as "therapeutically effective dose." Amounts effective for this use will depend on the age, weight and general condition of the subject/patient, and the like.

These nanotubes may be sterilized by conventional sterilization techniques, or may be sterile filtered. When employed as pharmaceuticals, the nanotubes of the subject invention are usually administered in the form of pharmaceutical compositions. This invention also includes pharmaceutical compositions comprising nanotubes, associated with one or more pharmaceutically acceptable carriers or excipients. The excipient is typically one suitable for administration to human subjects or other mammals. In making the compositions of this invention, the active ingredient is usually mixed with an excipient, and/or diluted by an excipient. When the excipient serves as a diluent, it can be a solid, semi-solid, or liquid material, which acts as a vehicle, carrier or medium for the active ingredient.

The nanotubes of the invention can be formulated so as to provide quick, sustained or delayed release of the active ingredient after administration to the patient by employing procedures known in the art.

Suitable methods and formulations for use in the present invention are found in REMINGTON'S PHARMACEUTICAL SCIENCES, Mace Publishing Company, Philadelphia, Pa., 17th ed. (1985).

According to one aspect of the invention, the nanotubes may be administered alone, or in combination with any other medicament. Thus, the formulation may comprise nanotubes in combination with another active ingredient, such as a drug, in the same formulation. When administered in combination, the nanotubes may be administered in the same formulation as other compounds as shown, or in a separate formulation. When administered in combination, the nanotubes may be administered prior to, following, or concurrently with the other compounds and/or compositions.

EXAMPLES

Example 1

Preparation of Nanotubes by Template Method

To prepare nanotubes using the template method, polycarbonate track etched membrane were immerse in methanol for 5 minutes. All of the methanol was drained off and then the membrane was immersed in a solution comprising 0.025 M $SnCl_2$ and 0.07 M trifluoroacetic acid. Both of these chemicals were added in equal volumes. The membrane was kept in the $SnCl_2$ and trifluoroacetic acid solution for 45 minutes. The solution was drained off and the membrane was immersed in methanol for two consecutive times, each for 2.5 minutes. The immersion of the membrane in methanol two consecutive times was done to remove any residual $SnCl_2$ or trifluoroacetic acid. The membrane was then immersed in an aqueous ammonical $AgNO_3$ solution for 5 minutes.

Next, the membrane was placed in a solution containing equal volumes of the following: 0.127 M of $Na_2SO_3$, 0.025 M of $NaHCO_3$, and 0.625 M of HCOOH and a commercial gold plating solution $Na_3Au(SO_3)_2$ (diluted from Oromerse Part B, Technic, Inc.). The solution was maintained at a temperature of about 5° C. The inner diameter of the tubes changed with the plating time. The membranes were kept in the gold-plating solution for 3, 6, 9 or 24 hours. After the respective amount of time, the solution was drained-off and $CH_2Cl_2$ was added to dissolve the membrane. The solution was then centrifuged to separate the aggregated nanotubes.

The solution was then carefully removed, leaving the aggregated nanotubes behind. About 2.5 mL of PEG was added to the aggregated nanotubes such that the PEG coated the nanotubes, causing the aggregated nanotubes to separate such that substantially individual nanotubes coated with PEG are available in water or similar solvent as a solution. The mixture was then vortexed (i.e., mixed vigorously using a genie vortexer or other similar mixer) to aid the coating of the nanotubes with PEG, increasing the availability of the nanotubes in solution.

The mixture was filtered using centricons by centrifugation to remove any particulate matter. The filtered nanotubes were then pelleted by centrifugation, the supernatant removed and the pellet re-suspended in 70% ethanol to remove excess PEG. The nanotubes were then pelleted again by centrifugation, the supernatant removed and the pellets are re-suspended in sterile water and stored at 4° C.

0.025 M of $SnCl_2$ was required. For a preparation of 100 ml, 0.948 gm of $SnCl_2$ was used, and for 40 ml, 0.3792 gm of $SnCl_2$ is used. The aqueous ammonical $AgNO_3$ solution was prepared by adding 0.0984 gm of $AgNO_3$, then adding a panel volume of 5 N NaOH drop-wise (if precipitating).

The resulting solution was used immediately. 0.07 M trifluoroacetic acid was used in an amount of 0.15964 gm or 0.104.33 μL. 0.127 M $Na_2SO_3$ was used in an amount of 0.32014 gm. 0.025 M $NaHCO_3$ was used in an amount of 0.04205 gm. 0.625 M formaldehyde was used in an amount of 0.3752 gm, wherein the total volume is 173.7 mL.

$CH_2Cl_2$ was added to dissolve the membrane. Sufficient $CH_2Cl_2$ (about 10 mL) was added to cover the membrane adequately and the resulting mixture is centrifuged and/or sonicated. Then, the nanotubes obtained from the membrane were again centrifuged and after separating the liquid, about 2-5 mL of PEG was added. Attomol can be added instead of PEG.

Before dissolving the membranes with $CH_2Cl_2$, as described above, the nanotubes were optionally coated with histidine by adding about 10 mL of a histidine solution such that the membranes are substantially immersed in the histidine. Further, acetic acid is added to balance the pH of the histidine solution. The membranes remain immersed in the histidine/acetic acid solution for a time sufficient to substantially coat the nanotubes.

Example 2

Preparation of Nanotubes using Histidine

The nanotubes were prepared using the method set forth in Example 1. Then the plated membranes were placed in a solution of histidine, and left in the solution for 24 hours, to allow the histidine to coat the inner walls of the nanotubes plated in the membranes. The coated membranes were removed and placed in $CH_2Cl_2$ and sonicated, to dissolve the membrane. PEG was added to the resultant solution to release the nanotubes into the PEG solution. The PEG solution was sonicated so that the nanotubes settled at the bottom. The PEG was removed so that the nanotubes could be collected. 70V EtOH was added, allowing the tubes to be suspended in a sterile medium. The solution was drained off after centrifuging, and then 70V EtOH was added to it.

Example 3

Preparation of Gold Nanotubes using Template Membranes

Materials used in this example included Polycarbonate Track Etched membranes (from Sterlitech™ Corporation); $SnCl_2$, ammonium hydroxide, tri-flouroacetic acid from Sigma Aldrich; L-Histidine, Stannous Chloride Anhydrous and Silver Nitride from Fluka; Sodium Sulfite Anhydrous and Sodium Bicarbonate from Mallinckrodt; Ormerse SO Part B™, commercial gold solution.

The procedure for the preparation of the gold nanotubes included immersing the polycarbonate track etched membrane in methanol for about 5 minutes. Substantially all of the methanol was drained off, and then the membrane was immersed in a solution which is 0.025 M in $SnCl_2$, i.e., 0.1896 gm for 20 mL of water and 0.07M in trifluoroacetic acid (ie;, 104.33 μL for 20 mL of water. Both the $SnCl_2$ and trifluoroacetic acid were added in equal volumetric proportions. The membrane was kept immersed in the $SnCl_2$ and trifluoroacetic acid solution for about 45 minutes. Then the liquid was drained off and the membrane immersed again in methanol for 2 consecutive times, each time for about 2.5 minutes to clean the membrane from the previously added chemicals. Aqueous ammonical AgNO$_3$ solution was added to the membrane and the membrane was left in the solution for about 5 minutes. The membrane was immersed in a solution at a temperature of 5° C. The solution contained 3 mL of each of the following: (i) 0.127 M of Na2SO$_3$, i.e., 0.32014 gm for a 20 mL solution; (ii) 0.025 M of NaHCO$_3$, i.e., 0.04205 gm for a 20 mL solution; 0.625 M of HCOOH, i.e., 347.4 µL for a 20 mL solution; commercial gold plating solution.

The inner diameter of the nanotubes changes with plating time. Therefore, the membranes were kept in the above solution for about 24 hours in order to achieve ideal proton conductance rates (i.e., the amount of mitochondrial uncoupling). After the respective amount of time, the solution was drained and CH$_2$Cl$_2$ was added to dissolve the membrane. Then the solution was centrifuged so that the nanotubes settled down at the bottom. PEG was added to the solution and the resultant solution was stored at 4° C. The liquid was then filtered through a 0.08 µm filter so that the fine nanotubes without any residue (particulate matter) could be collected.

Example 4

Coating the Nanotubes with Histidine

After obtaining the nanotubes prepared in Example 3, histidine was added as an aqueous solution to the nanotubes and centrifuged at a very low speed for about 5 minutes. The solution was vortexed a few times to ensure that the histidine coated the nanotubes. Then the procedure of Example 2 was followed.

Instead of using the 0.08 µm filter in Example 3, larger filters can be used having a size ranging between 0.001 µm and 0.1 µm.

Example 5

In Vitro Study of Interaction of Nanotubes with Mitochondria

Mitochondria were prepared from adult Sprague-Dawley rats and nanotubes obtained from the above examples (both histidine-coated and uncoated tubes) where added to examine state 3 and state 4 respiration rates of the mitochondria and the effect of the nanotubes were measured.

| | |
|---|---|
| 08/24 | 1 animal |
| 08/25 | 1 |
| 08/30 | 1 |
| 08/31 | 1 |
| 09/02 | 1 Mito resp + NT EM PIC |

The mitochondria were prepared by Ficoll preparation and then the mitochondria were collected for respiration, ethyl ester of tetramethylrhodamine (TMRE) based membrane potential estimation and especially for electron micrograph pictures.
Samples for EM
1. Control—mitochondria without nanotubes (ethanol 75%) or for the EM control included the addition of nanotubes that had been made in the absence of PEG such that the nanotubes were not soluble and where filtered out of the solution.

2. Mitochondria with nanotubes that were plated for different times or in the absence or presence of histidine. Following measurements of mitochondrial respiration the samples were pelleted by centrifugation and processed for EM.

Example 6

Figure 2:
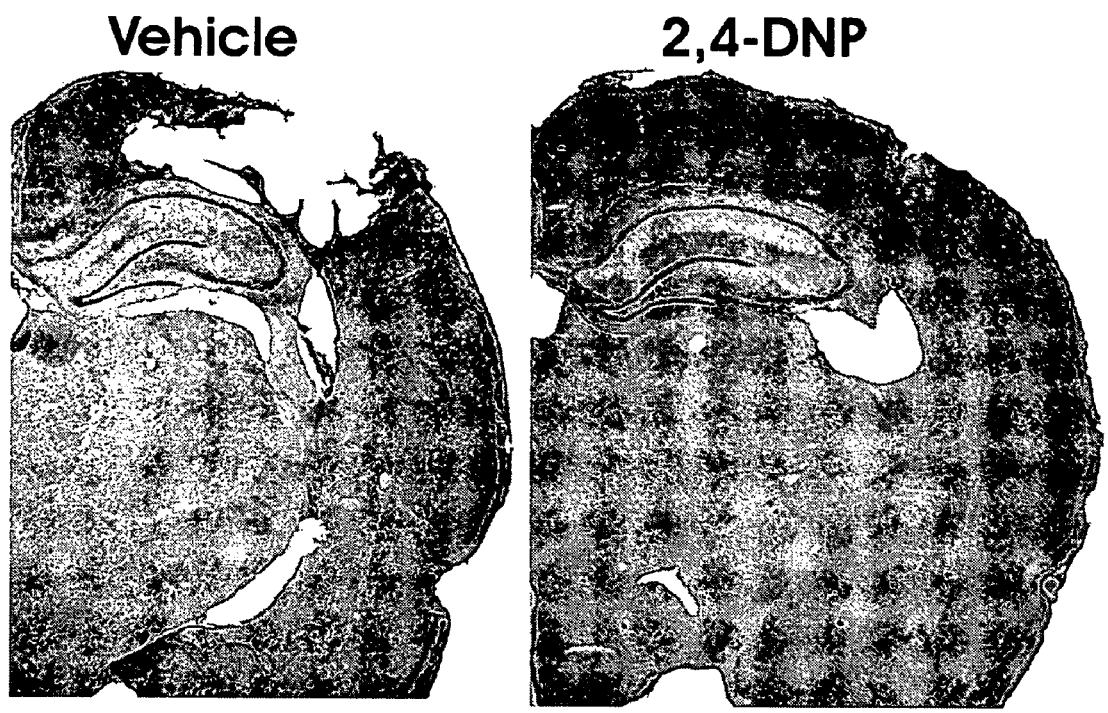
FIG. 2 shows bar graphs that illustrate mitochondrial uncoupling as a result of administering 2,4-DNP increases tissue sparing following traumatic brain injury.
Figure 2:
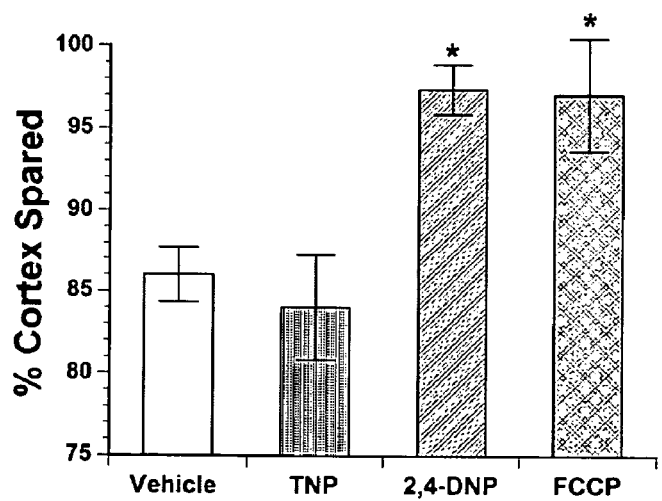

As shown in FIG. 2, mitochondrial uncoupling increases tissue sparing following traumatic brain injury. Adult Sprague-Dawley rats received a moderate injury (about 1.5 mm compression of the cortex) and were administered either vehicle (DMSO), 5 mg/kg of 2,4-DNP, 2.5 mg/kg FCCP or 6.2 mg/kg of at 5 min post-injury. Representative sections from an injured 2,4-DNP-treated animals and vehicle-treated at 15 days post-injury are shown in panel A. The mitochondrial uncouplers 2,4-DNP and FCCP significantly increased tissue sparing compared to vehicle-treated animals. In contrast, administration of TNP, an ananlogue of 2,4-DNP that does not uncouple mitochondria, had no significant effect on tissue sparing. Bars represent group means, SD (n=6/group) and * indicates p<0.01 compared to vehicle treated animals.

Example 7

Figure 3:
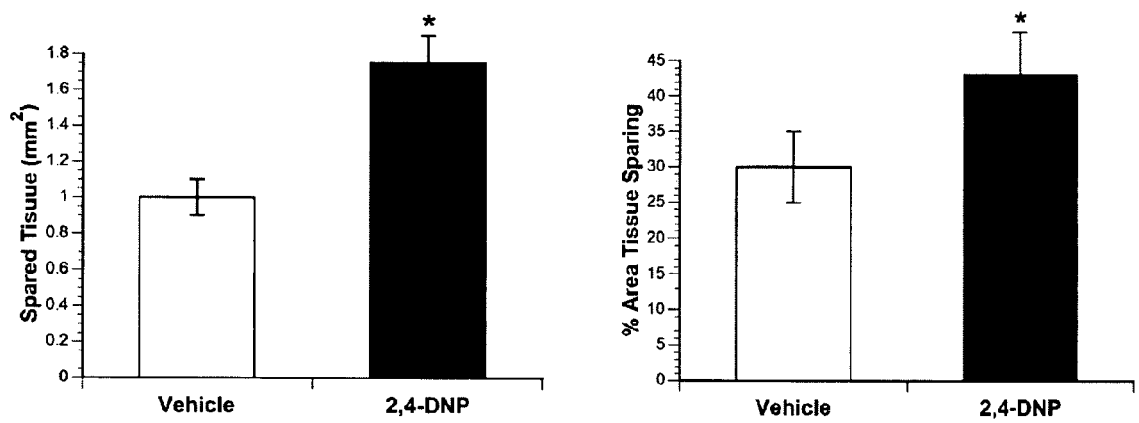
FIG. 3 shows bar graphs that illustrate post-injury administration of 2,4-DNP increases tissue sparing following spinal cord injury ("SCI").

As shown in FIG. 3, post-injury administration (15 mins post-injury) of 5 mg/kg of 2,4-DNP increases tissue sparing following SCI. Bar graphs representing the extent of tissue sparing measured through cross-sections of the T10 segment injury epicenters 48 hours after a moderate (150 kydn) contusion SCI. The 2,4-DNP-treated groups showed significantly greater sparing compared to the vehicle (DMSO) treated animals through the lesion epicenters. The significantly greater cross-sectional area of tissue preservation with both treatments (left graph) was reflected in a significantly higher percentage of tissue sparing at the lesion epicenters compared to vehicle controls (right graph). The lesion epicenter means were derived from sections in each cord demonstrating the least spared tissue. Bars represent group means, SEM (n=5-6/group). Using an unpaired t-test, * indicates p<0.05 compared to vehicle-treated groups.

Example 8

Figure 4:
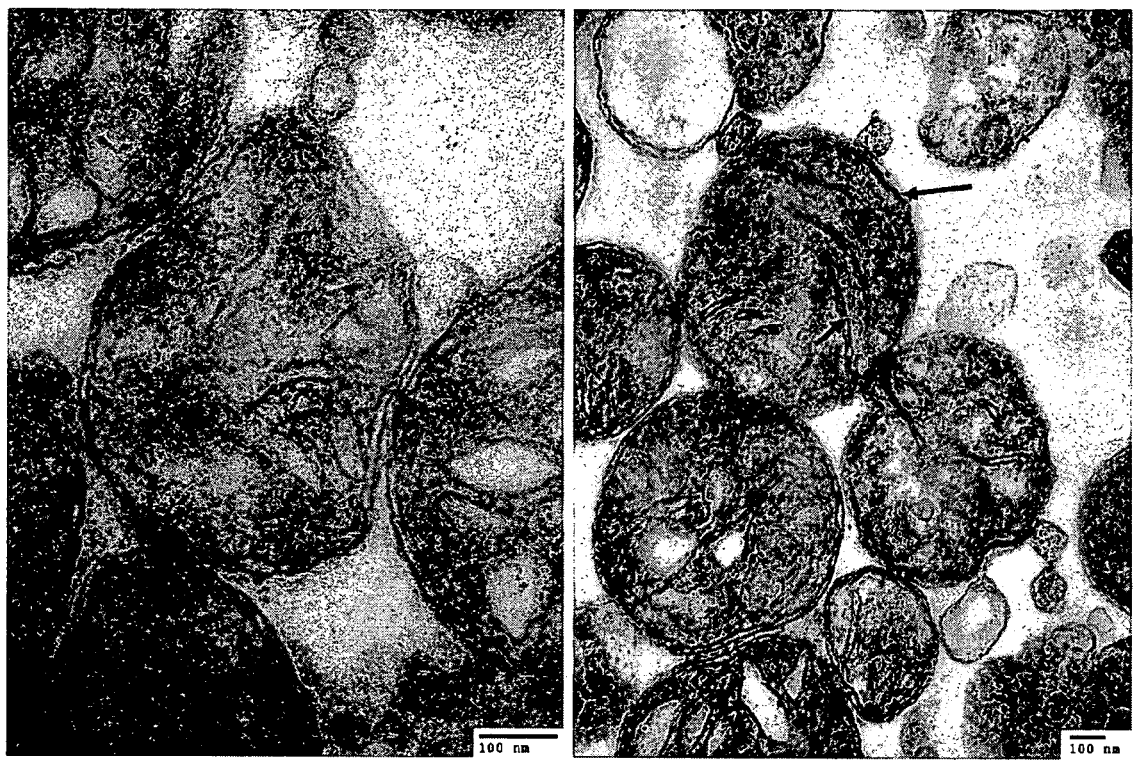
FIG. 4 shows electron microscopy photomicrographs of isolated cortical mitochondrial following the addition of nanotubes (24 hour+histidine) that were made in the presence (left panel) or absence (right panel) of PEG.

FIG. 4 shows electron microscopy photomicrographs of cortical mitochondria isolated from adult Sprague-Dawley rats (näive) following the addition of nanotubes (24 hr+histidine) that were made in the presence of PEG (right panel) and in the absence of PEG (left panel). PEG is coated on the outside of the nanotubes in order to allow them to become soluble in solution by breaking up the aggregated nanotubes into individually PEG coated nanotubes. The PEG coated nanotubes can be filtered and administered. Nanotubes that are manufactured in the absence of PEG do not make it through the filtration process. In the right panel, nanotubes are evident as the dense, dark particles and as indicated by the arrows can be found in both the cristae (i.e., folded inner membrane) and outer membrane of the mitochondria. The presence of the intact outer and inner membranes also indicates that nanotubes do not alter the ultrastructure of the mitochondria.

Example 9

Figure 5:
FIG. 5 shows a higher magnification of isolated cortical mitochondrial following the addition of nanotubes (24 hour+ histidine) that were made in the presence of PEG.

FIG. 5 shows a higher magnification of cortical mitochondria isolated from adult Sprague-Dawley rats (näive) following the addition of nanogtubes (24 hr+histidine) that were made in the presence of PEG. This image illustrates the location of the nanotubes (dark, dense spots) in the mitochondria and the arrowhead indicates a nanotube located in the cristae (inner membrane of mitochondria).

Example 10

Figure 6:
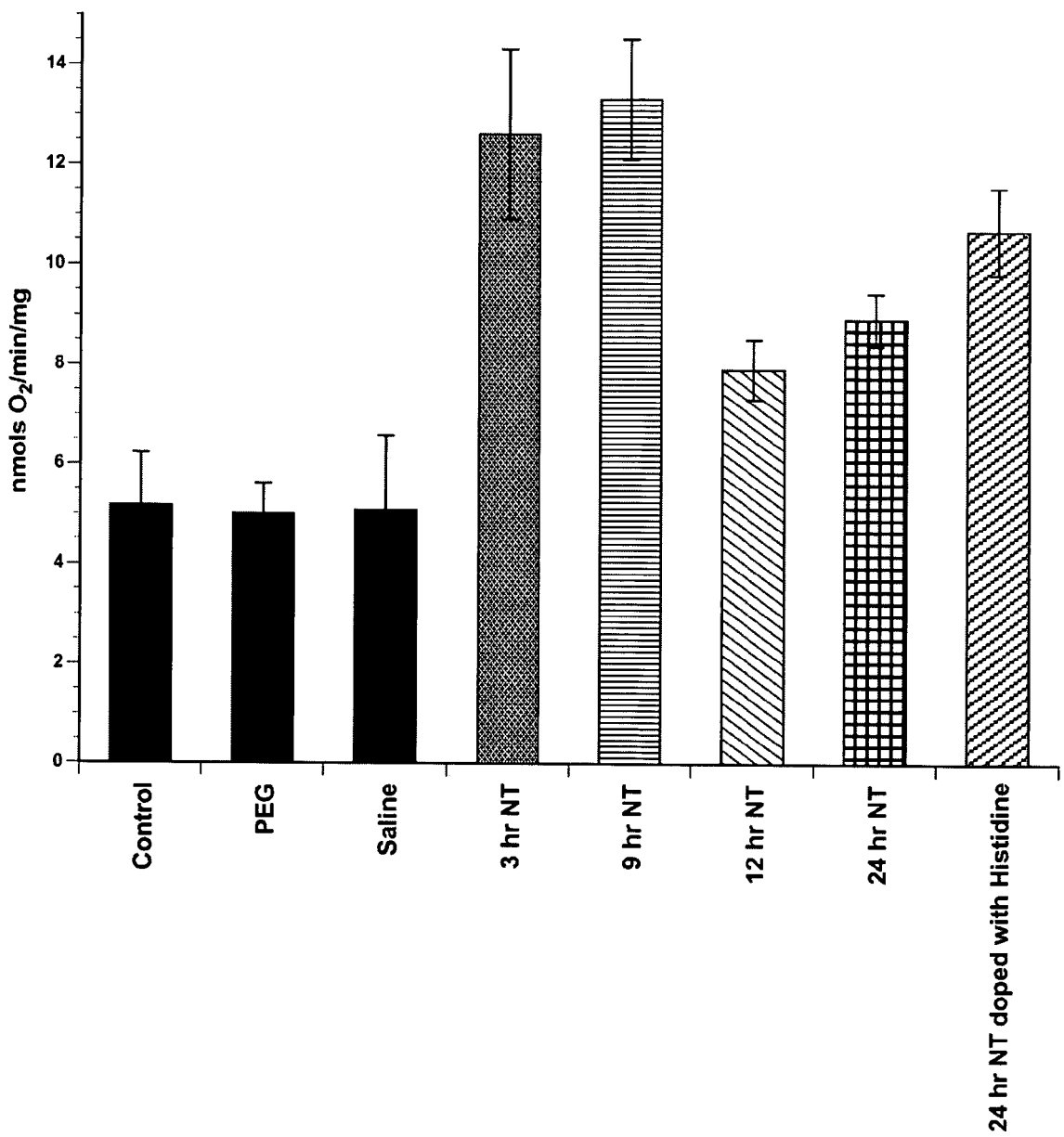
FIG. 6 is a bar graph that shows that mitochondrial respiration is increased as a function of nanotube plating time (the longer the plating the time the smaller the diameter of the nanotube) and/or the "doping" of the inside of the nanotube with compounds of specific pKas.

The bar graph depicted in FIG. 6 shows that mitochondrial respiration is increased as a function of nanotube plating time (i.e., the longer the plating time the smaller the i.d. of the nanotube) and/or the "doping" of the inside of the nanotube with compounds of specific pkas. Mitochondrial respiration was measured using standard oxymetric techniques in cortical mitochondria isolated from adult Sprague-Dawley rats (näive) to determine if nanotubes would increase respiration and uncouple mitochondria. As shown in FIG. 4, short plating times increased the amount of mitochondrial respiration and oxygen consumption. All measurements were made in the presence of oligomycin, which is an inhibitor of the mitochondrial ATP synthase, to induce state IV respiration, which is the state of respiration in which mitochondria utilize the minimal amount of oxygen and protons cannot cross the inner membrane of the mitochondria. The data shown in FIG. 4 is expressed as nmols of oxygen consumed per minute per mg of mitochondrial protein. Bars are group means, SEM, (n=4-5/group).

Example 11

Figure 7:
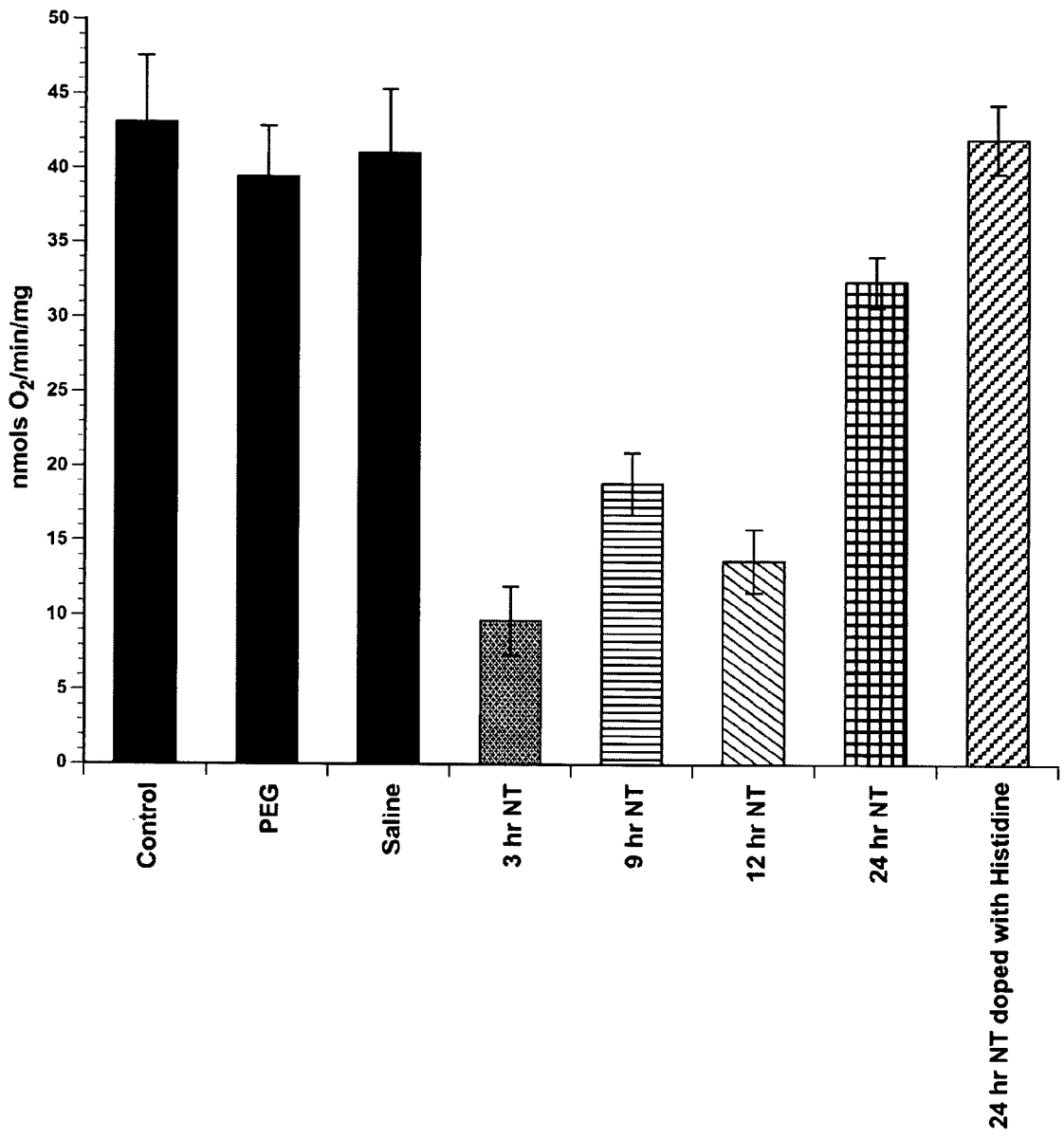
FIG. 7 shows nanotubes manufactured by plating for 24 hrs and/or "doped" with histidine do not impair mitochondrial ATP production.

FIG. 7 shows nanotubes (labeled as "NT" in FIG. 5) manufactured by plating for 24 hrs and/or "doped" with histidine do not impair mitochondrial ATP production. All assays were performed during state III respiration which is induced by the addition of ADP to cortical mitochondria isolated from adult Sprague-Dawley rats (näive) and oxygen consumption was measured as the mitochondria converted ADP into ATP. The data shown in FIG. 5 is expressed as nmols of oxygen consumed per minute per mg of mitochondrial protein. As shown in FIG. 5, the nanotubes increased respiration/metabolism without reducing mitochondrial ATP production. Bars are group means, SEM, (n=6/group).

Example 12

Figure 8:
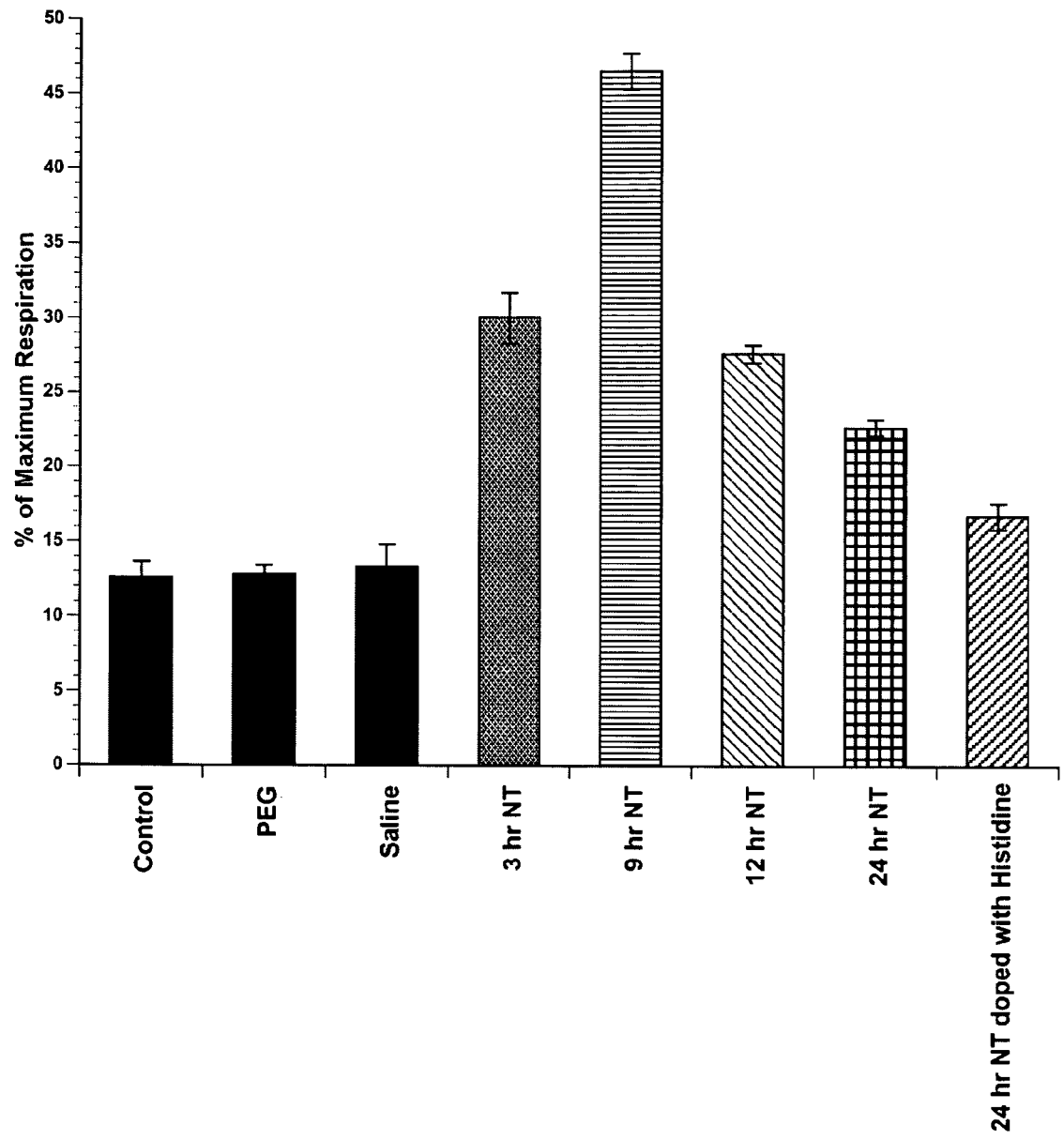
FIG. 8 shows nanotubes manufactured by plating nanotubes for 24 hrs and/or doping them with histidine increase respirations less than nanotubes manufactured for shorter times.

FIG. 8 shows nanotubes (labeled as "NT" in FIG. 6) manufactured by plating nanotubes for 24 hrs and/or doping them with histidine increase respirations less than nanotubes manufactured for shorter times. Mitochondria were isolated from adult Sprague-Dawley rats (näive) and mitochondrial oxygen consumption was measured following the addition of the various nanotubes and compared to maximum oxygen consumption induced by the addition of the chemical mitochondrial uncoupler FCCP. The data shown in FIG. 6 is expressed as the % of FCCP-induced maximum oxygen consumption (respiration). Bars are group means, SEM, (n=6/group).

Example 13

Figure 9:
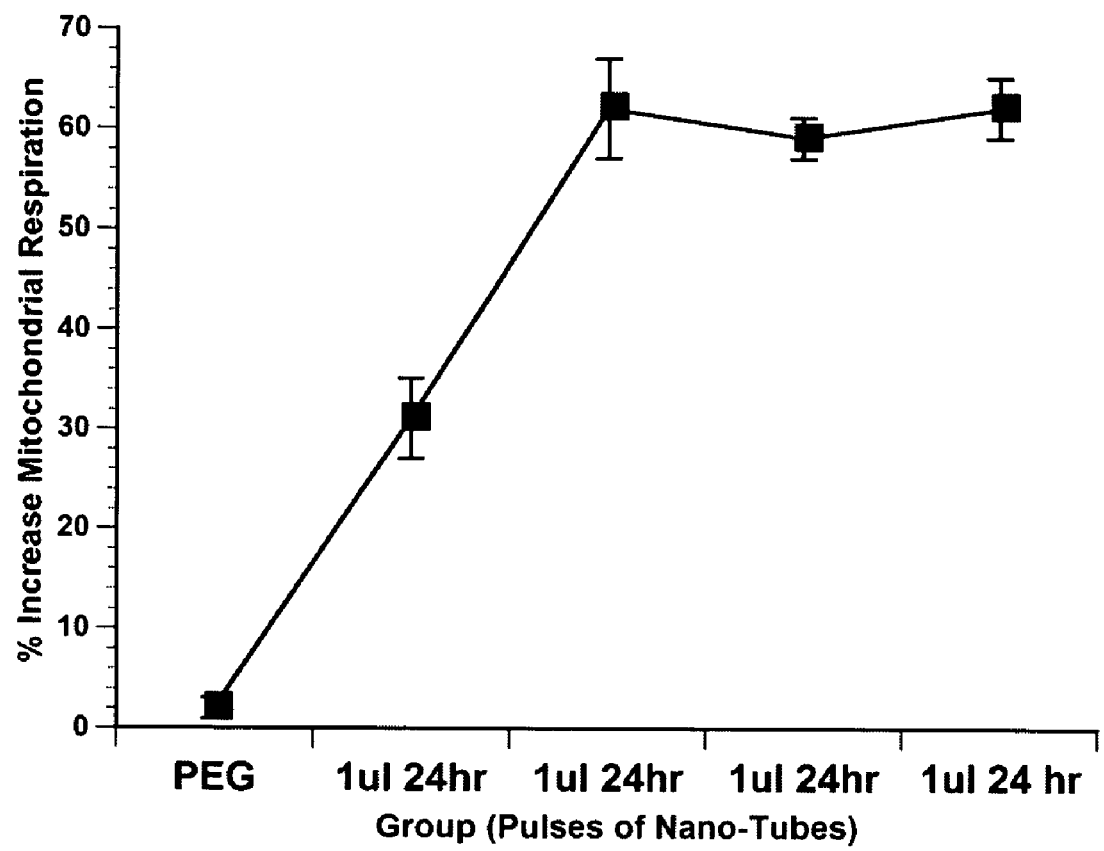
FIG. 9 shows that sequential additions of nanotubes results in a saturation point being reached due the self-rectifying nature of the nanotubes.

FIG. 9 shows that sequential additions of nanotubes results in a saturation point being reached due the self-rectifying nature of the nanotubes. In other words, once a saturation point is reached (i.e., enough nanotubes have been added to uncouple all the mitochondria present in the preparation) no more increase in respiration occurs since the nanotubes shut themselves off to proton flow when membrane potential drops below threshold (as discussed above). Mitochondrial respiration (oxygen consumption) was measured in cortical mitochondria isolated from adult Sprague-Dawley rats (näive) that were locked in state IV respiration using oligomycin. To begin the experiment a 1 μl addition of PEG, which functions as a vehicle or carrier for the nanotubes, was added followed by four-1 μl additions of nanotubes every 5 minutes. The data shown in FIG. 7 is expressed as the % increase in respiration compared to state IV respiration. Points are group means, SEM, (n=3 individual experiments.

Example 14

Figure 10:
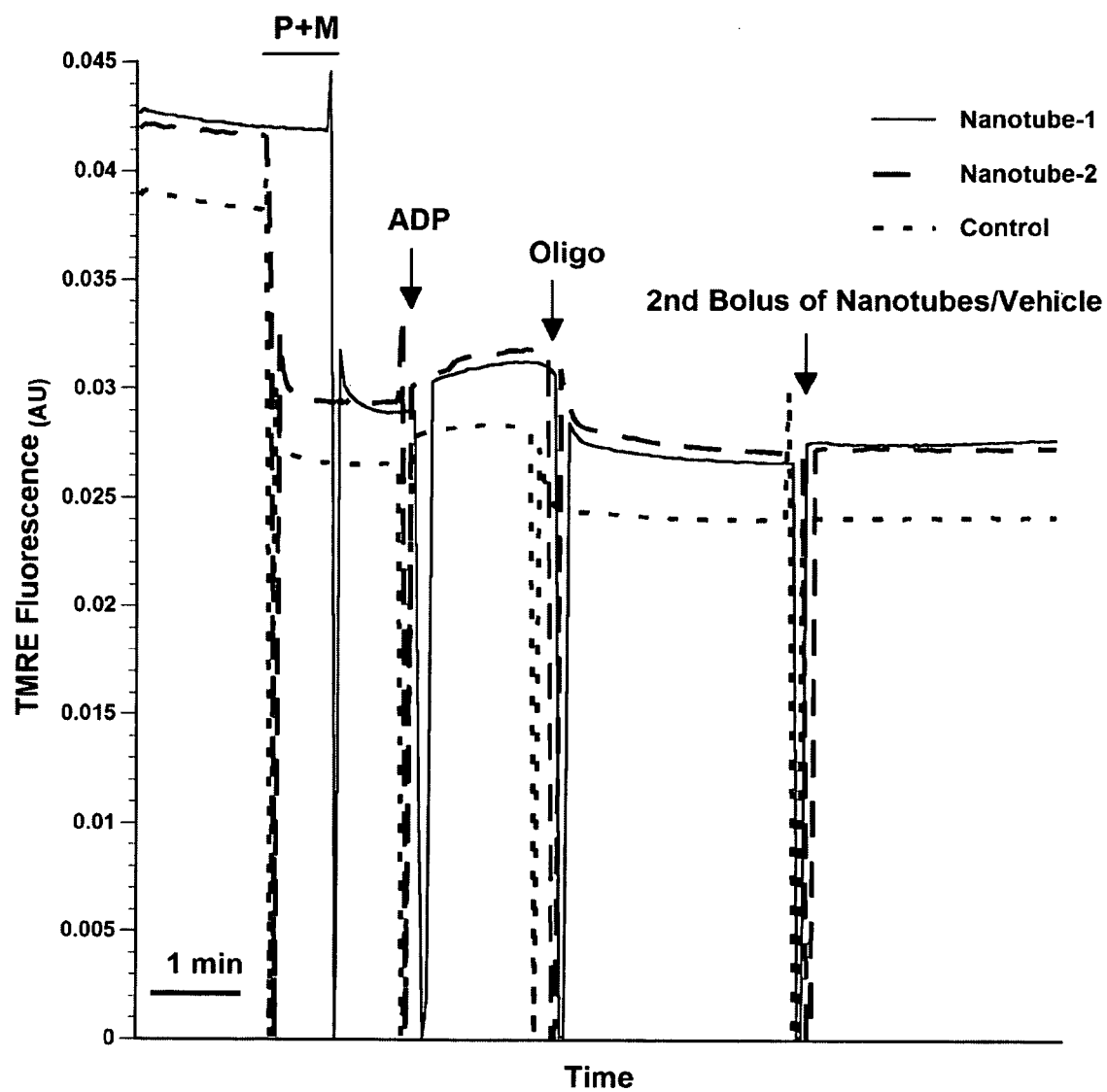
FIG. 10 shows that nanotubes reduce mitochondrial membrane potential which explains their ability to increase respiration, oxygen consumption and metabolism.

FIG. 10 shows that nanotubes reduce mitochondrial membrane potential which explains their ability to increase respiration, oxygen consumption, and metabolism. Cortical mitochondria isolated from adult Sprague-Dawley rats (näive) were used for the experiments summarized in FIG. 8, which utilized the cationic membrane potential fluorescent indicator TMRE. TMRE, due to its positive charge, is sequenced into the mitochondrial matrix following the addition of pyruvate and malate (P+M), which results in a reduction in fluorescent signal. Compared to the control samples (in which an equal volume of saline was added to the buffer), nanotubes (plated 24 hr+histidine) reduce the mitochondrial membrane potential evident by the increase in TMRE signal illustrated in all conditions. This is due to less membrane potential being available to drive the uptake of TMRE into the mitochondrial matrix treated with the nanotubes.

It should be noted that mitochondria treated with nanotubes respond substantially the same way to all other conditions expect for the lower membrane potential. It should further be noted that an additional bolus of nanotubes did not affect membrane potential showing that the nanotubes are self-rectifying. The steep deflections are artifact caused by the opening of the spectrofluormeter door to make additions to the chamber which allows light from the room to enter the spectrofluormeter chamber.

Example 15

Figure 11:
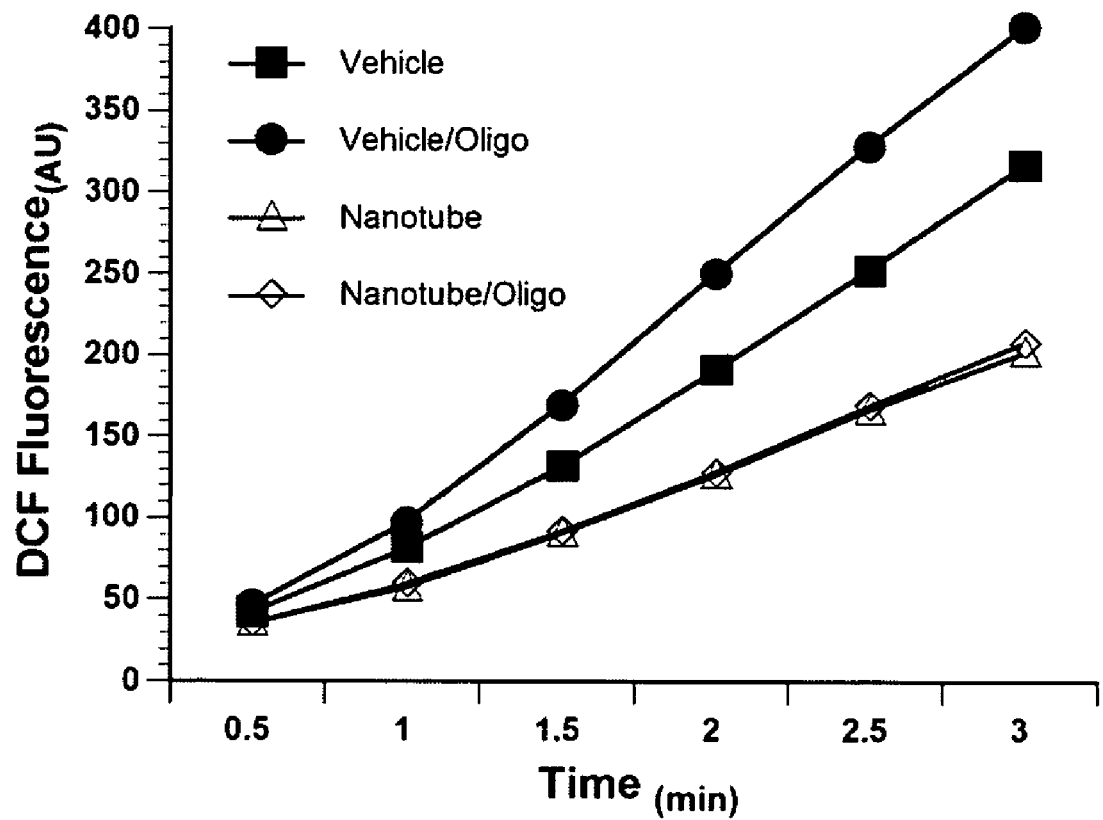
FIG. 11 shows that nanotubes reduce reactive oxygen species production in isolated mitochondria.

FIG. 11 shows that nanotubes reduce reactive oxygen species production in isolated mitochondria. Mitochondria are the primary source of reactive oxygen species in cells as electrons slip from the electron transfer chain and reduce oxygen to superoxide. Cortical mitochondria were isolated from adult Sprague-Dawley rats (näive) and reactive oxygen species production measured using the fluorescent indicator DCF, which fluoresces when oxidized leading to an increase in signal. Mitochondrial reactive oxygen species were assessed under both basal conditions and in the presence of oligomycin to maximize membrane potential and reactive oxygen species production. Nanotubes reduced both basal and maximal reactive oxygen species produced by mitochondria.

Example 16

Figure 12:
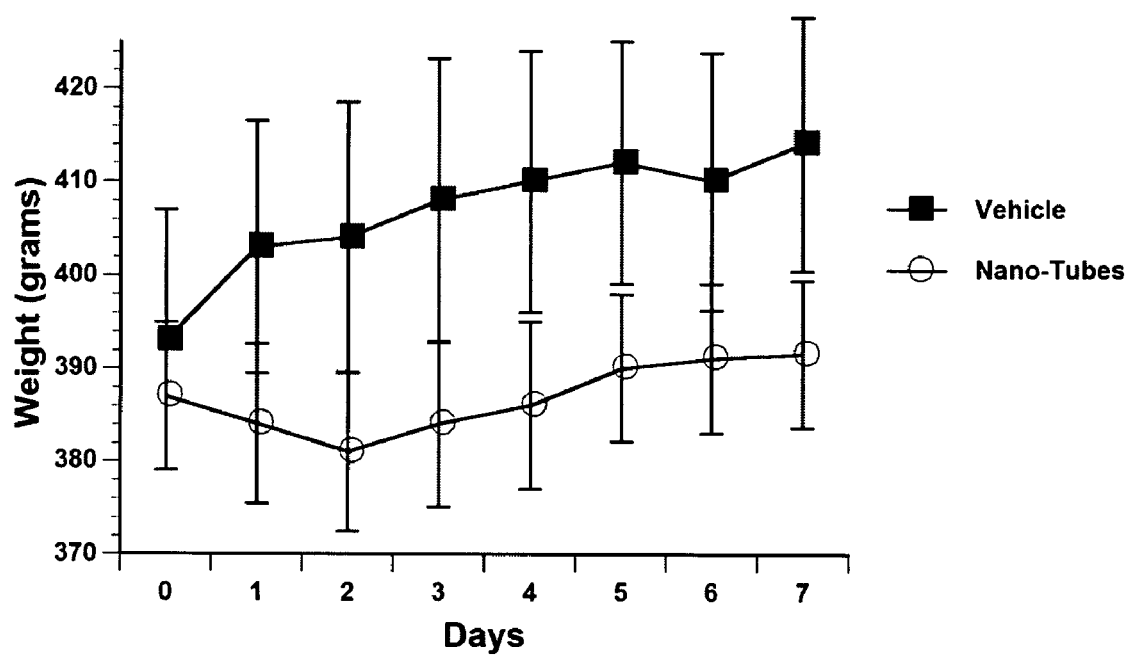
FIG. 12 shows a line graph of days v. grams of weight gained upon administering nanotubes compared to administering vehicle controls over a period of seven days.

FIG. 12 shows that animals injected with nanotubes stop gaining weight compared to vehicle controls. Adult Sprague-Dawley rats were administered either saline or 2.7 mg/kg nanotubes intraperitoneally following weighing on day 0. The animals were then weighed everyday at the same time for 7 days. Food and water intake did not differ between the groups and no toxic side-effects in either group was noted (e.g., panting, ruffled fur, vocalization, etc.). All the animals in the groups were considered to be in good health. On average the saline-treated animals increased their body weight by ~5-6% over the 8 day period whereas the nanotube-treated animals showed less than 1% gain in body weight over the same period of time.

Figure 13:
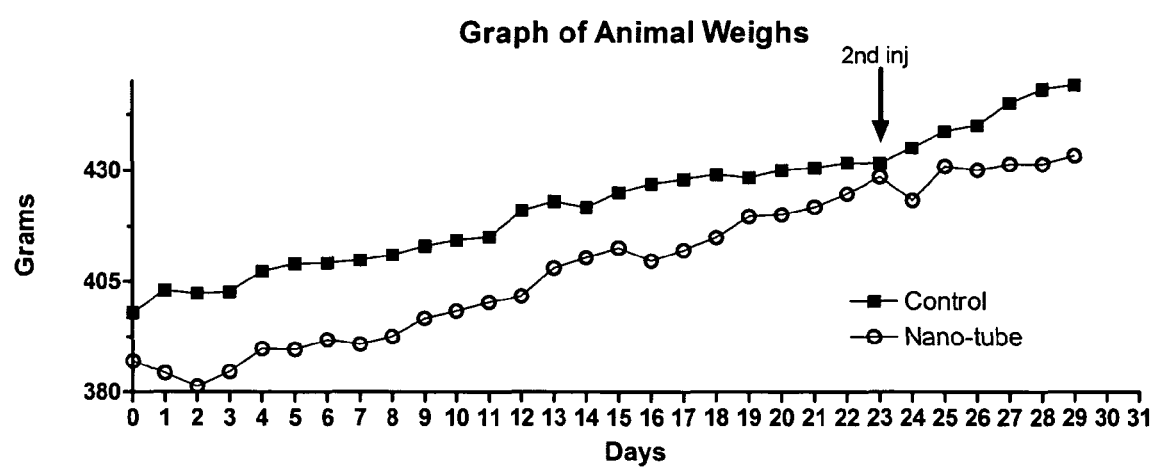
FIG. 13 shows a line graph of days v. grams of weight gained upon administering nanotubes compared to administering vehicle controls over a period of 31 days.

As shown in FIG. 13, adult Sprague-Dawley rats were injected with nanotubes at day 0 and then again on day 23 to determine the effective half-life of the nanotubes in vivo. Adult Sprague-Dawley rats were administered intraperitoneally either saline (i.e., Control) or nanotubes (2.7 mg/kg) following weighing on day 0. The animals were then weighed everyday at the same time for 31 days. Food and water intake did not differ between the groups and no toxic side-effects in either group was noted (e.g., panting, ruffled fur, vocalization, etc.) and all the animals were considered to be in good health.

Still referring to FIG. 13, 8 days after the first injection the nanotube treated animals began to gain weight at a rate similar to that measured in control animals, indicating that the nanotubes were no longer uncoupling mitochondria and raising metabolism. 23 days after the initial injection of nanotubes we administered the same dosage of nanotubes to the animals or administered saline to the control animals. Again the nanotube-treated animals lost weigh and weight gain was halted compared to control animals. Data points are the group means (n=3/group).

While this invention has been particularly shown and described with references to preferred embodiments thereof, it will be understood by those skilled in the art that various changes in form and details may be made therein without departing from the spirit and scope of the invention as defined by the appended claims.

All references cited and/or discussed above are herein incorporated by reference in their entirety.

What is claimed is:

1. A method of uncoupling mitochondria in a subject comprising: administering nanotubes to the subject in a therapeutically effective amount, wherein the nanotubes are self-rectifying nanotubes, having a length of less than 50 nm and a conductance such that the nanotubes conduct protons only where a proton gradient of about 120-220 mV is present.

2. The method of claim 1, wherein the nanotubes are coated with a pKa reducing compound.

3. The method of claim 1, wherein the subject is a mammal.

4. The method of claim 1, wherein the nanotubes have an inner diameter suitable for uncoupling mitochondria.

5. The method of claim 1, wherein the nanotubes have an inner diameter which allows the nanotubes to self-rectify.

6. The method of claim 1, wherein the nanotubes comprise metals or polymers.

7. The method of claim 6, wherein the metal is gold or silver.

8. The method of claim 6, wherein the polymers are natural polymers or synthetic polymers.

9. The method of claim 6, wherein the polymers are selected from the group consisting of poly(vinyl alcohol), poly(esters), polyglycolide, polycaprolactone, polyethylene oxide), poly(butylene terephthalate), poly(hydroxyalkanoates), hydrogels, modified poly(saccharides), starch, cellulose, chitosan and combinations thereof.

10. A method of decreasing reactive oxygen species and decreasing detrimental loading of $Ca^{2+}$ into mitochondria of a subject comprising: administering nanotubes to the subject in a therapeutically effective amount, wherein the nanotubes are self-rectifying, having a length of less than 50 nm and having a conductance such that the nanotubes conduct protons only where a proton gradient of about 120-220 mV is present.

11. The method of claim 10, wherein the subject is a mammal.

12. The method of claim 10, wherein the nanotubes have an inner diameter designed for uncoupling mitochondria.

13. The method of claim 10, wherein the nanotubes have an inner diameter which allows the nanotubes to self-rectify.

14. The method of claim 10, wherein the nanotubes comprise metals or polymers.

15. The method of claim 14, wherein the metal is gold or silver.

16. The method of claim 14, wherein the polymers are natural polymers or synthetic polymers.

17. The method of claim 14, wherein the polymers are selected from the group consisting of poly(vinyl alcohol), poly(esters), polyglycolide, polycaprolactone, poly(ethylene oxide), poly(butylene terephthalate), poly(hydroxyalkanoates), hydrogels, modified poly(saccharides), starch, cellulose, and chitosan.

18. The method of claim 1 wherein the nanotubes are less than 20 nm in length.

19. The method of claim 10 wherein the nanotubes are less than 20 nm in length.

20. The method of claim 1 wherein the nanotubes are coated with polyethylene glycol or surrounded by lipid microspheres.

21. The method of claim 10 wherein the nanotubes are coated with polyethylene glycol or surrounded by lipid microspheres.

* * * * *